United States Patent [19]

Kudryk et al.

[11] Patent Number: 5,876,947
[45] Date of Patent: Mar. 2, 1999

[54] MONOSPECIFIC ANTIBODY REACTIVE WITH FIBRINOGEN AND FIBRINOPEPTIDE B

[75] Inventors: Bohdan J. Kudryk, Hillsdale, N.J.; Colvin M. Redman, Franklin Square; Jian-Zhong Zhang, New York, both of N.Y.

[73] Assignee: The New York Blood Center, Inc., New York, N.Y.

[21] Appl. No.: 900,660

[22] Filed: Jul. 25, 1997

[51] Int. Cl.$^6$ ......................... G01N 33/53; G01N 33/543; G01N 33/536; C07K 16/36

[52] U.S. Cl. ......................... 435/7.1; 424/9.1; 424/133.1; 424/139.1; 424/145.1; 435/7.92; 435/13; 435/69.6; 435/70.21; 435/240.27; 435/972; 435/975; 436/516; 436/518; 436/524; 436/528; 436/530; 436/531; 436/538; 436/548; 530/387.3; 530/387.9; 530/388.25; 530/391.1; 935/15; 935/104; 935/107; 935/108

[58] Field of Search ..................................... 435/7.1, 7.24, 435/7.8, 7.92, 7.93, 7.94, 7.95, 13, 70.21, 172.2, 240.27, 69.6; 436/516, 518, 524, 528, 529, 530, 531, 534, 538, 548, 69; 935/15, 100, 104, 107, 108; 530/387.3, 387.9, 388.25, 389.3, 391.1, 391.3; 424/133.1, 9.1, 139.1, 145.1

[56] References Cited

FOREIGN PATENT DOCUMENTS 0 345 811 B1  12/1989  European Pat. Off. .

OTHER PUBLICATIONS

Eckhardt et al., 1981. Measurement of desarginine fibrinopeptide B in human blood. J. Clin. Invest. 67:809–816.

Wilner et al., 1979. Immunochemical analysis of rqabbit antihuman fibrinopeptide B antibodies. Biochemistry 18:5078–5082.

Campbell, 1991. *Monoclonal Antibody and Immunosensor Technology*, Elsevier, Amsterdam. pp. 3–6, 20–23, 42–45.

Chung et al., 1983. Characterization of complementary deoxyribonucleic acid and genomic deoxyribonucleic acid for the β chain of human fibrinogen. Biochemistry 22:3244–3250.

Harlow et al., 1988. *Antibodies. A Laboratory Manual*, Cold Spring Harbor Laboratory, Cold Spring Harbor. pp. 72–77, 600–612.

Owens et al., 1994. The genetic engineering of monoclonal antibodies. J. Immunological Methods 168: 149–165.

Kinjoh et al., 1994. Production of a monoclonal antibody against rabbit fibrinopeptide B (FPB) for immunological assay of rabbit FPB. Japanese Journal of Physiology 44 (Supp. 1): S117, Abstract#272.

Bilezikian, SB, Nossel HL, Butler VP and Canfield RE, "Radioimmunoassay of human fibrinopeptide B and kinetics of fibrinopeptide cleavage by different enzymes," *J. Clinical Investigation* 56:438–445 (1975).

Bini A, Callender S, Procyk R, Blombäck B and Kudryk BJ, "Flow and antibody binding properties of hydrated fibrins prepared from plasma, platelet rich plasma and whole blood," *Thrombosis Res* 76(2):145–156 (1994).

Bini A, Fenoglio JJ Jr, Mesa–Tejada R, Kudryk B and Kaplan KL, "Identification and distribution of fibrinogen, fibrin, and fibrin(ogen) degradation products in atherosclerosis," *Arteriosclerosis* 9(1):111–121 (1989).

Bini A, Fenoglio JJ Jr, Sobel J, Owen J, Fejgl M and Kaplan KL, "Immunochemical characterization of fibrinogen, fibrin I and fibrin II in human thrombi and atherosclerotic lesions," *Blood* 69(4):1038–1045 (1987).

Bini A, Itoh Y, Kudryk BJ and Nagase H, "Degradation of cross–linked fibrin by matrix metalloproteinase 3 (stromelysin 1): Hydrolysis of γGly404–Ala405 peptide bond," *Biochemistry* 35(40):13056–13063 (1996).

Bini A and Kudryk BJ, "Fibrin and its derivatives in the normal and diseased vessel wall," *Ann NY Acad Sci* 667:112–126.

Bini A, Mesa–Tejada R, Fenoglio JJ Jr, Kudryk B and Kaplan KL, "Immunohistochemical characterization of fibrin(ogen)–related antigens in human tissues using monoclonal antibodies," *Laboratory Investigation* 60(6):814–821 (1989).

Collen D and Lijnen HR, "Basic and clinical aspects of fibrinolysis and thrombolysis," *Blood* 78(12):3114–3124 (1991).

Fu Y and Grieninger G, "Fib$_{420}$: A normal human variant of fibrinogen with two extended α chains," *Proc Natl Acad Sci USA* 91:2625–2628 (1994).

Fu Y, Weissbach L, Plant PW, Oddoux C, Cao Y, Liang TJ, Roy SN, Redman CM and Grieninger G, "Carboxy–Termina–Extended variant of the human fibrinogen α subunit: a novel exon conferring marked homology to β and γ subunits," *Biochemistry* 31(48):11968–11972.

Koopman J, Haverkate F, Grimbergen J, Egbring R and Lord ST, "Fibrinogen Marburg: A homozygous case of dysfibrinogenemia, lacking amino acids Aα 461–610 (Lys 461 AAA → Stop TAA)," *Blood* 80(8):1972–1979 (1992).

(List continued on next page.)

*Primary Examiner*—James C. Housel
*Assistant Examiner*—James L. Grun
*Attorney, Agent, or Firm*—Hoffmann & Baron, LLP

[57] ABSTRACT

The invention provides monospecific antibodies that are specifically reactive with fibrinopeptide B (FPB) and with fibrinogen and fragments thereof containing the amino acid sequence defined by SEQ ID NO:1. The invention also provides anti-FPB probes, including monospecific anti-FPB antibodies that have been detectably labeled. In addition, the invention provides methods of using the monospecific antibodies for detection of fibrinopeptide B, as well as reagents and kits for performing the methods. For example, the invention provides a method for detecting fibrinopeptide B with specificity in biological samples such as blood samples, by using the antibody to immunometrically bind to the fibrinopeptide B. Diagnostic methods for determining information associated with atherogenesis and/or thrombogenesis. The invention further provides continuous cell lines (hybridomas) that produce monospecific anti-FPB antibodies.

34 Claims, 11 Drawing Sheets

OTHER PUBLICATIONS

Kudryk B, Bini A, Procyk R, Matsueda GR and Shainoff JR, "Cross–linking of fibrinogen by tissue transglutaminase: Involvement of the C–termini of the Aα– and γ–chains in formation of Aαγ–dyads," *Thromb Haemostas* 69(6):1260 (1993).

Kudryk, B, Gidlund M, Rohoza A, Ahadi M, Coiffe D and Weitz JI, "Use of a synthetic homologue of human firbinopeptide A for production of a monoclonal antibody specific for the free peptide," *Blood* 74(3):1036–1044 (1989).

Kudryk BJ, Grossman ZD, McAfee JG and Rosebrough SF, "Monoclonal antibodies as probes for fibrin(ogen) proteolysis," *Monoclonal Antibodies in Immunoscinitgraphy* J–F. Chatal, ed. CRC Press, Boca Raton 365–398 (1989a).

Kudryk B, Robinson D, Netre C, Hessel B, Blombäck M, and Blombäck B, "Measurement in human blood of fibrinogen/fibrin fragments containing the Bβ15–42 sequence," *Thromb Res* 25:277–291 (1982).

Kudryk B, Rohoza A, Ahadi M, Chin J and Wiebe ME, "A monoclonal antibody with ability to distinguish between $NH_2$–terminal fragments derived from fibrinogen and fibrin," *Mol Immunol* 20:1191–1200 (1983).

Kudryk B, Rohoza A, Ahadi M, Chin J, and Wiebe ME, "Specificity of a monoclonal antibody for the $NH_2$–terminal region of fibrin," *Mol Immunol* 21:89–94 (1984).

Kudryk B, Rohoza A, Ahadi M, Gidlund M, Procyk R and Matsueda GR, *Thromb Haemostas* 65:898 (Abstract 714) (1991).

Liu CY, Sobel JH, Weitz JI, Kaplan KL, and Nossel HL, "Immunologic identification of the cleavage products from the A alpha– and B beta–chains in the early stages of plasmin digestion of fibrinogen," *Thromb Haemostas* 56(1):100–106 (1986).

Loike JD, Sodeik B, Cao L, Leucona S, Weitz JI, Detmers PA, Wright SD and Silverstein SC, "CD11c/CD18 on neutrophils recognizes a domain at the N terminus of the A–alpha chain of fibrinogen," *Proc Natl Acad Sci USA* 88:1044–1048 (1991).

Plow EF and Edgington TS, "Surface markers of fibrinogen and its physiologic derivatives revealed by antibody probes," *Semin Thromb Haemostas* 8(1):36–56 (1982).

Procyk R, Kudryk B, Callender S, Blombäck B, "Accessibility of epitopes on fibrin clots and fibrinogen gels," *Blood* 77: 1469–1475 (1991).

Singer II, Kawka DW, Bayne EK, Donatelli SA, Weidner JR, Williams HR, Ayala JM, Mumford RA, Lark MW, Glant TT, Nabozny GH and David CS, "VDIPEN, A metalloproteinase–generated neoepitope, is induced and immunolocalized in articular cartilage during inflammatory arthritis," *J Clinical Investigation, Inc.* 95:2178–2186 (1995).

Valenzuela R, Shainoff JR, DiBello PM, Urbanic DA, Anderson JM, Matsueda GR and Kudryk BJ, "Immunoelectrophoretic and immunohistochemical characterizations of fibrinogen derivatives in atherosclerotic aortic intimas and vascular prosthesis pseudo–intimas," *Amer J Pathol* 141(4):861–880 (1992).

Weissbach L and Grieninger G, "Bipartite mRNA for chicken α–fibrinogen potentially encodes an amino acid sequence homologous to β– and γ–fibrinogens," *Proc Natl Acad Sci USA* 87:5198–5202 (1990).

Protein Stained Gel

Immunoblot (T54-2)

Immunoblot (P10)

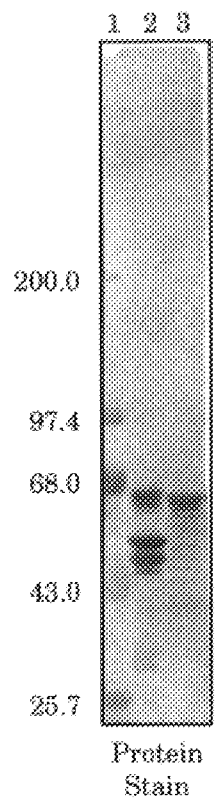 FIG-2A Protein Stain
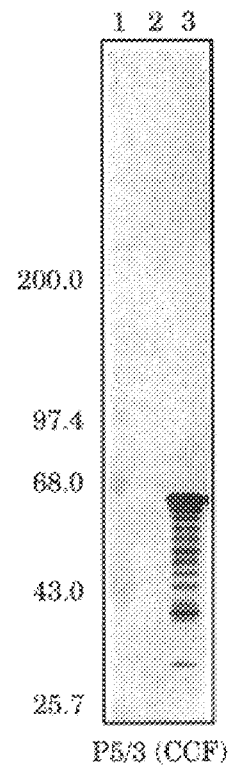 FIG-2B P5/3 (CCF)
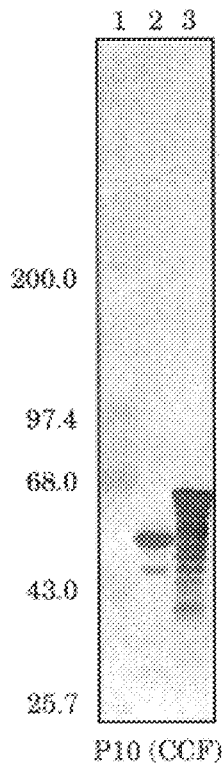 FIG-2C P10 (CCP)

P10 (CCF)
4-chloro-1-naphthol
substrate

P10 (CCF)
chemiluminescent
substrate

FIG-5

FUSION PROTEIN

```
            Xa              Bβ 1-13
             ↓
MBP........IEGR ISEFQGVNDNEEGFFSAQGVNDN
            vector-                    SEQ ID
            derived aa                  NO:6
```

PEAK I PEPTIDES(S)

[Factor Xa-cleaved, amylose resin non-adsorbed peptide(s)]

| sequence cycle | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| | E | | | | | | | | | | | | | | |
| | 355 | | | | | | | | | | | | | | |
| | G | V | N | D | N | E | E | G | F | F | S | A | Q | G | V |
| | 372 | 342 | 218 | 143 | 199 | 156 | 155 | 173 | 146 | 134 | 51 | 88 | 47 | 28 | 17 |
| | I | S | E | F | Q | G | V | N | D | N | E | E | G | F | F |
| | 151 | 50 | 88 | 71 | 60 | 62 | 58 | 50 | 29 | 34 | 28 | 28 | 30 | 25 | 26 |

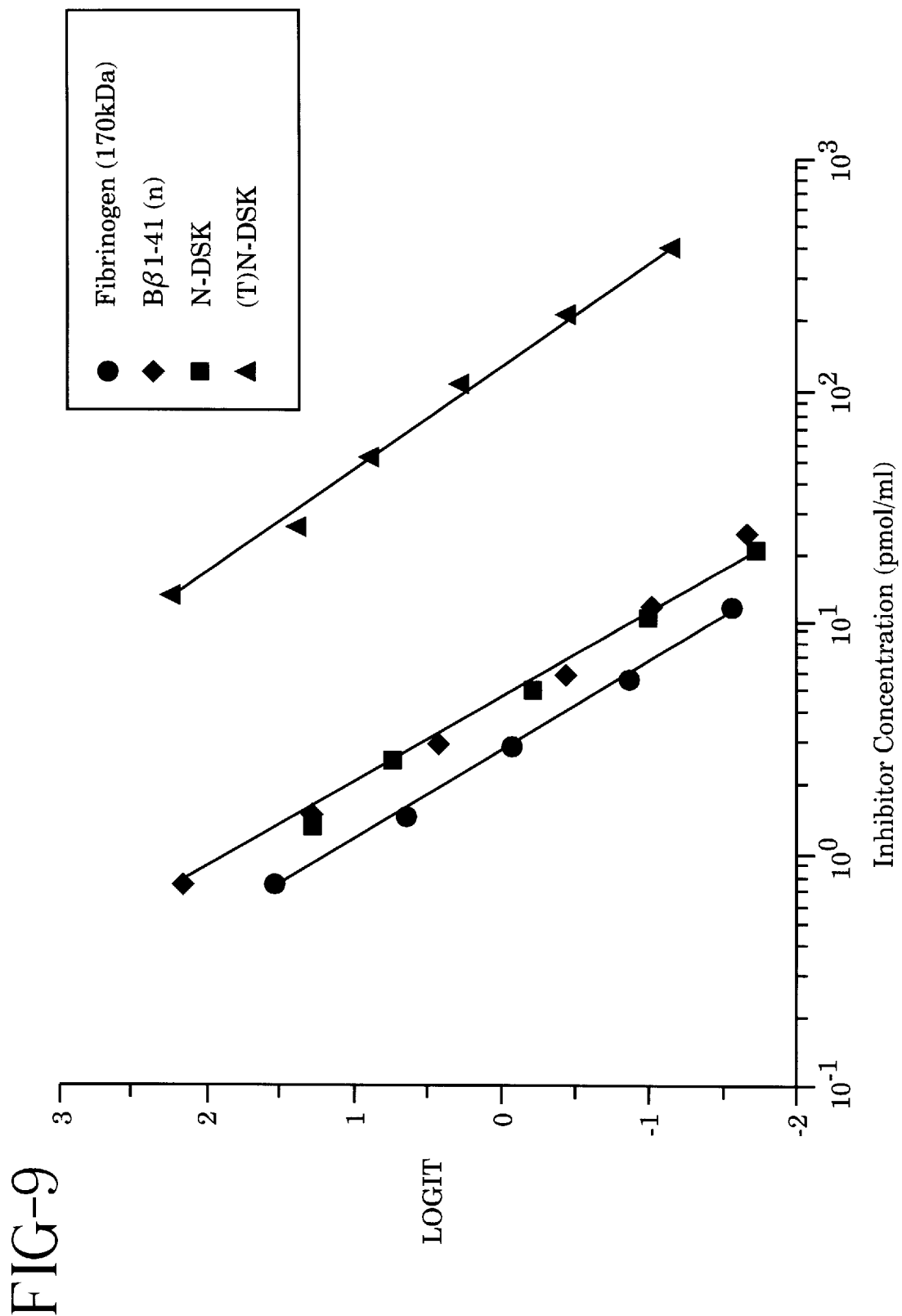

MONOSPECIFIC ANTIBODY REACTIVE WITH FIBRINOGEN AND FIBRINOPEPTIDE B

This invention was made in part with Government support under NIH Grant No. HL37457 awarded by the National Institutes of Health. The Government has certain rights in this invention.

BACKGROUND OF THE INVENTION

This invention relates to probes for, and methods of, detecting and measuring enzyme-mediated digestion of fibrinogen. More particularly, the invention relates to an antibody specifically reactive with a domain of fibrinogen and with a metabolic product of fibrinogen degradation, and a method of use of the antibody.

The clotting of blood is part of the body's natural response to injury or trauma, and is crucial to stopping loss of blood in such situations. Blood clot formation derives from a series of events called the coagulation cascade, the final steps of which involve the formation of the enzyme thrombin. Thrombin converts circulating fibrinogen into fibrin, a mesh-like structure that forms the insoluble framework of the blood clot. The hemostasis enabled by clot formation is often a life-saving process in response to trauma, serving to arrest the flow of blood from severed vasculature.

The life-saving process of clot generation in response to an injury can, however, become life-threatening when it occurs at inappropriate places in the body or at inopportune moments. For example, a clot can obstruct a blood vessel and thereby reduce or stop the supply of blood to an organ or other body part. In addition, the deposition of fibrin contributes to partial or complete stenosis of blood vessels, resulting in chronic diminution of blood flow. Equally life-threatening are clots that become detached from their original sites and flow through the circulatory system causing blockages at remote sites. Such clots are known as embolisms. Indeed, pathologies of blood coagulation, such as heart attacks, strokes, and the like, have been estimated to account for approximately fifty percent of all hospital deaths.

Fibrinogen is one of the more well-studied and abundant proteins in the human circulatory system. By the late 1960s, the general subunit structure of fibrinogen was firmly established (Blombäck 1968) and, a decade later, the complete amino acid sequence was reported (Lottspeich et al. 1977; Henschen et al. 1977; Henschen et al. 1979; Doolittle et al. 1979). Over the next 10 years, the cluster of three separate genes encoding the $\alpha$ (alpha), $\beta$ (beta), and $\gamma$ (gamma) subunits was identified on chromosome 4q23-q32 (Kant et al. 1985), and the apparently complete genetic sequences of all three fibrinogen subunits were published (Chung et al. 1991).

Fibrinogen (also abbreviated herein as "Fg") is a heavily disulfide-bonded homodimeric protein, composed of two symmetrical units (monomers), each including single copies each or three polypeptide chains: the A$\alpha$ (alpha), B$\beta$ (beta), and $\gamma$ (gamma) chains. Thus, fibrinogen has the generic structure $(A\alpha B\beta\gamma)_2$. For a review see Doolittle (1987). All three of the fibrinogen subunits have coiled domains, which permit the subunits to engage one another to form a "coiled coil" region in the fibrinogen monomer. In addition, the B$\beta$ and $\gamma$ chains each have a globular domain, while the A$\alpha$ chain is present in two forms; a predominant form having no corresponding globular domain (A$\alpha$), and a less prevalent form in which a globular domain is present (A$\alpha_E$) (Fu et al. 1992; 1994). Accordingly, because fibrinogen is homodimeric and because two forms of the A$\alpha$ subunit have been identified, two principal forms of fibrinogen are recognized: $(A\alpha B\beta\gamma)_2$ and $(A\alpha_E B\beta\gamma)_2$.

Fibrinogen's complex structure, and its central role in blood clot formation and wound healing account for the high profile it has enjoyed as a subject of both biochemical and medical research. Recently, new attention has been given to structure/function relationships in the fibrinogen molecule. This new interest has in part been prompted by growth in the understanding of this protein's range of activity in normal and pathological states (Blombäck 1991; Bini et al. 1992; Dvorak 1992). Moreover, antibodies have been developed that are specifically reactive with or specifically bind to only some of the fragments, thereby permitting molecular identification of certain fragments with great accuracy and precision (Kudryk et al. 1989a). While a monoclonal antibody with specificity for human fibrinopeptide A has been identified (Kudryk et al. 1989b; see also European Patent Specification EP 0 345 811 B1), no comparable probe specific for fibrinopeptide B has yet been reported. However, despite these advances, the complexity of fibrinogen and its metabolic system have to date eluded complete elucidation.

Fibrinogen is synthesized and secreted into the circulation by the liver. Circulating fibrinogen is polymerized under attack by thrombin to form fibrin, which is the major component of blood clots or thrombi. Subsequently, fibrin is depolymerized under attack by plasmin to restore the fluidity of the plasma. Many of the steps in the polymerization and depolymerization processes have been well established (Doolittle 1984). The elevated levels of fibrinogen that are part of the acute phase response occurring in the wake of infections and trauma are now known to come from increased hepatic production, primarily in response to interleukin-6 (IL-6) (Sehgal et al. 1989).

The degradation of fibrinogen through hydrolytic cleavage by thrombin yields two forms of fibrin. The first form, "fibrin I," is defined by thrombin-mediated cleavage of the $\alpha$ chain (or the "A$\alpha$" chain) at A$\alpha$16–17. This cleavage releases two short N-terminal peptides designated "fibrinopeptide A" or "FPA" (A$\alpha$1–16). Subsequently, thrombin cleaves the $\beta$ chain (or the "B$\beta$" chain) at B$\beta$14–15 to create "fibrin II." The cleavage of the B$\beta$ chain at B$\beta$14–15 releases a peptide known as "fibrinopeptide B" or "FPB" consisting of the first 14 amino acid residues of the B$\beta$ chain (B$\beta$1–14). See Blombäck (1991). It is only after the thrombin cleavage of fibrinogen that the polymerization of fibrin occurs. Fibrinopeptide B, especially, is closely related to onset of fibrin polymerization.

In wound repair, fibrinogen serves as a key protein, achieving rapid arrest of bleeding following vessel injury. It promotes both the aggregation of activated platelets with one another to form a hemostatic plug, as well as endothelial cell binding at the site of injury to seal the margins of the wound. As the most abundant adhesive protein in the blood, fibrinogen attaches specifically to platelets, endothelial cells and neutrophils via different integrins (Hynes 1992). Five putative receptor recognition domains on human fibrinogen, distributed over its three subunits, have been identified by in vitro and in vivo analyses (Kloczewiak et al. 1984; Cheresh et al. 1989; Loike et al. 1991; Farrell et al. 1992; Gonda et al. 1982; Ribes et al. 1989).

Elevated levels of fibrinogen have been found in patients suffering from clinically overt coronary heart disease, stroke and peripheral vascular disease. Although the underlying mechanisms remain speculative, recent epidemiological studies leave little doubt that plasma fibrinogen levels are an independent cardiovascular risk factor possessing predictive power that is at least as high as that of other accepted risk factors such as smoking, hypertension, hyperlipoproteinemia or diabetes (Ernst 1990; Ernst et al. 1993). The structure of fibrin has been analyzed extensively in vitro (Doolittle 1984). Only recently, however, has attention been paid to the molecular structure of human thrombi and atherosclerotic plaques with respect to fibrinogen and fibrin products (Bini et al. 1987). Whereas thrombi formed in vivo consist primarily of fibrin II cross-linked by factor XIIIa, fibrinogen itself is a major component of uncomplicated atherosclerotic lesions, particularly fibrous and fatty plaques. Immunohistochemical as well as immunoelectrophoretic analyses indicate that fibrinogen in the aortic intima is comparatively well protected from thrombin and plasmin, and that much of it is deposited through direct cross-linking by tissue transglutaminase without becoming converted to fibrin (Valenzuela et al. 1992). Further understanding of these issues awaits the development of methods for the differential determination of fibrinogen subtypes in medical samples.

Fibrinogen-derived protein is also a major component of the stroma in which tumor cells are embedded, but little is known about its molecular structure. Tumor cells promote the secretion of potent permeability factors that cause leakage of fibrinogen from blood vessels (Dvorak et al. 1992). Extravascular clotting occurs due to procoagulants associated with tumor cells. The resulting fibrinogen/fibrin matrix is constantly remodeled during tumor growth as a consequence of fibrinolysis induced by tumor cell-derived plasminogen activators. It is assumed that fibrin/fibrinogen degradation products play a role during escape of metastatic tumor cells from the primary tumor. There are indications that integrin $\alpha_v\beta_3$, which is known to interact with the RGDS site in the C-terminal region of the $\alpha$ chain, may be an important tumor cell surface receptor since it is preferentially expressed on invasive melanoma (Felding-Habermann et al. 1992).

From the foregoing discussion, it becomes clear that significant gaps exist in the understanding of the thrombotic process. Intelligent management of patients depends upon accurate and precise understanding of their thrombotic states. The present state of the art lacks the probes and methods necessary to enable such determinations.

As a result, there exists a need for highly specific, sensitive and reproducible probes for enhancing the understanding of the structure and function of fibrinogen, especially in relation to the generation and function of fibrinopeptides A and B by thrombin cleavage. Accordingly, there exists a need for probes suitable for the specific detection and purification of fibrinopeptide B and fibrinogen incorporating the peptide. In addition, means for diagnostic testing of subjects with respect to the amount and distribution of fibrinogen in the body, as well as monitoring of the generation of fibrinopeptide B as an index of in vivo thrombin activity (i.e., thrombotic state), are needed. The present invention effectively addresses these and other needs for the first time.

SUMMARY OF THE INVENTION

The present invention provides, inter alia, a monospecific antibody, that binds specifically with an epitope defined by an amino acid sequence SEQ ID NO:1. The monospecific antibody can bind specifically with fibrinogen and fragments thereof comprising the amino acid sequence defined by SEQ ID NO:1. In particular, the antibody can bind specifically with fibrinopeptide B or des-Arg fibrinopeptide B. Also, the antibody can bind with the N- or $NH_2$-terminal "disulfide knot" of fibrinogen cleaved by cyanogen bromide (CNBr) (abbreviated "N-DSK" (A$\alpha$1–51, B$\beta$1–118, $\gamma$1–78)$_2$, $M_r$=58,000).

Preferably, the monospecific antibody is detectably labeled by conjugation to a detectable moiety. The detectable moiety can be selected from the group consisting of radionuclides, enzymes, specific binding pair components, colloidal dye substances, fluorochromes, reducing substances, latexes, digoxigenin, metals, particulates, dansyl lysine, antibodies, protein A, protein G, electron dense materials, and chromophores.

The monospecific antibody may be attached to a substrate. Suitable substrates can include a component selected from the group consisting of gels, hydrogels, resins, beads, nitrocellulose, nylon filters, microtiter plates, culture flasks, and polymeric materials.

The monospecific antibody of the invention may comprise an antigen-binding region, which may be selected from the group consisting of Fab, F(ab')$_2$, and Fv fragments.

The monospecific antibody may be a modified, synthetic, recombinant, or chimeric antibody. Preferably, the antibody is a monoclonal antibody. More preferably, the antibody is a monoclonal antibody produced by the hybridoma cell line identified as P10.

The invention also provides a composition for binding fibrinogen or a fibrinopeptide B, comprising a monospecific antibody that binds specifically with an epitope defined by an amino acid sequence SEQ ID NO:1. The monospecific antibody may also bind specifically with fibrin(ogen) and fragments thereof comprising the amino acid sequence defined by SEQ ID NO:1. For example, the monospecific antibody in the composition binds specifically with fibrinopeptide B and des-Arg fibrinopeptide B. Also, the antibody in the composition binds specifically with the N-DSK fragment of fibrinogen cleaved by cyanogen bromide.

Preferably, composition includes a monospecific antibody that is detectably labeled by conjugation to a detectable moiety. Again, the detectable moiety for labeling the antibody can be selected from the group consisting of radionuclides, enzymes, specific binding pair components, colloidal dye substances, fluorochromes, reducing substances, latexes, digoxigenin, metals, particulates, dansyl lysine, antibodies, protein A, protein G, electron dense materials, and chromophores.

Alternatively, the composition may include a monospecific antibody attached to a substrate. Suitable substrate can include a component selected from the group consisting of gels, hydrogels, resins, beads, nitrocellulose, nylon filters, microtiter plates, culture flasks, and polymeric materials.

The monospecific antibody in the composition may comprise an antigen-binding region, and the antigen-binding region may selected from the group consisting of Fab, F(ab')$_2$, and Fv fragments. The monospecific antibody may be a modified, synthetic, recombinant, or chimeric antibody. Preferably, the monospecific antibody in the composition is a monoclonal antibody. More preferably, the monospecific antibody is a monoclonal antibody produced by the hybridoma cell line identified as P10.

The composition may further comprise a differentiating component that binds with fibrinogen or a subunit or fragment thereof For example, the composition may include a differentiating antibody (a second antibody), that has specificity for another domain of fibrinogen.

The invention further provides a method of detecting fibrinogen or a fragment thereof comprising an amino acid sequence defined by SEQ ID NO:1, the method comprising:

contacting a testable system with a composition comprising a monospecific antibody that binds specifically with an epitope defined by an amino acid sequence SEQ ID NO:1, and measuring specific binding of the antibody in the testable system; wherein specific binding of the antibody in the testable system is associated with the presence of fibrinogen in the sample.

Accordingly, the method may be selected from the group consisting of enzyme-linked immunosorbent assay methods, immunonephelometry methods, agglutination methods, precipitation methods, immunodiff-usion methods, immunoelectrophoresis methods, immnunofluorescence methods, radioimmunoassay methods, and immunohistochemistry methods.

In the method, the monospecific antibody may be detectably labeled by conjugation to a detectable moiety as described above. Alternatively, the monospecific antibody may be attached to a substrate, as described above.

The monospecific antibody useful according to the method may comprise an antigen-binding region, such as an antigen-binding region selected from the group consisting of Fab, F(ab')$_2$, and Fv fragments. The method can also employ a monospecific antibody that is a modified, synthetic, recombinant, or chimeric antibody. Preferably, the monospecific antibody is a monoclonal antibody, more preferably, the antibody is a monoclonal antibody produced by the hybridoma cell line identified as P10.

The invention further provides a kit for the detection of fibrinogen or a fragment thereof, comprising:

(a) a composition comprising a monospecific antibody that binds specifically with an epitope defined by an amino acid sequence SEQ ID NO:1; and (b) a container housing the composition.

The kit may include a monospecific antibody that is detectably labeled by conjugation to a detectable moiety, as described. The kit may include a monospecific antibody that is attached to a substrate.

Preferably, the monospecific antibody of the kit is a monoclonal antibody, more preferably, the antibody is a monoclonal antibody produced by the hybridoma cell line identified as P10.

Furthermore, the invention provides a method for diagnosing the presence or probability of thrombogenesis or atherogenesis in a subject, comprising:

(a) measuring an amount of protein comprising an amino acid sequence defined by SEQ ID NO:1 in a subject by means of a composition comprising a monospecific antibody that binds specifically with an epitope defined by an amino acid sequence SEQ ID NO:1;

(b) comparing the measured amount of the protein for the subject with an amount of the protein recognized to have an association with thrombogenesis or atherogenesis; and (c) determining from the comparison the presence or probability of thrombogenesis or atherogenesis in the subject.

In addition, the invention provides a continuous cell line, that produces a monoclonal antibody that specifically binds with an epitope defined by an amino acid sequence SEQ ID NO:1. A highly preferred continuous cell line a hybridoma cell line identified as P10.

As a result of the invention, the artisan is now enabled to specifically detect an important enzyme-cleavage product of fibrin(ogen), which permits the accurate and precise determination of the thrombotic status of individuals. Methods are provided for detecting the peptide product by means of a monospecific antibody, and a variety of related immunological applications permit determination of the presence of the peptide product in biological samples of many types. Thus, the artisan's ability to diagnose and treat thrombolytic disorders is significantly advanced.

These and other advantages of the present invention will be appreciated from the detailed description and examples that are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein:

FIG. 2A is an electrophoretic separation of protein samples, stained for protein; FIG. 2B is a Western blot using a P5/3 antibody-based probe; FIG. 2C is a Western blot using a P10-based probe.

FIG. 5 is a table showing the amino acid sequence of a portion of the MBP-FPB fusion protein, with sequencing data given below for two peptides obtained through selective cleavage of the fusion protein.

FIG. 9 is a graph illustrating a competition ELISA using the P10 antibody.

DETAILED DESCRIPTION OF THE INVENTION

Figure 1A:
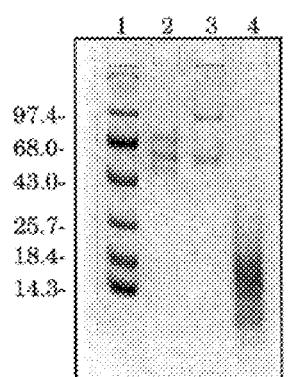
FIG. 1A is an electrophoretic separation of protein samples, stained for protein.

It is known that, due to the fluidity and complexity of the physiology of fibrin formation and degradation, many forms of fibrin and fibrinogen are present in the circulating blood as well as in thrombotic and atherosclerotic lesions. The many forms of these molecules result from continual assault by proteolytic enzymes that variously cleave the molecules.

This invention provides the skilled artisan with a singularly useful tool for assessing the thrombotic status of patients in the clinical setting. The antibody of the invention is exquisitely sensitive to fibrinopeptide B and des-Arg FPB, both of which are significant metabolites of fibrinogen, a protein known to characterize thrombotic state. As a result, the antibody of the invention enables precise and accurate detection of fibrinopeptide B and des-Arg FPB, resulting in an objective measure of the thrombotic status of the patient.

Human fibrinopeptide B (hFPB; Bβ1–14) is defined by the amino acid sequence: QGVNDNEEGFFSAR (SEQ ID NO:4), but is typically observed as ZGVNDNEEGFFSAR (SEQ ID NO:5) with its cyclised N-terminal pyroglutamic acid (abbreviated "Z"). However, it is known from experimentation that when exogenous hFPB is added to blood, most of the peptide is converted in a very short time to a metabolite des-Arg/hFPB, by the elimination of the C-terminal arginine. Human des-Arg Fibrinopeptide B (des-Arg hFPB; Bβ1–13) is defined by the amino acid sequence: QGVNDNEEGFFSA (SEQ ID NO:2), or more typically ZGVNDNEEGFFSA (SEQ ID NO:3). The conversion of hFPB to des-Arg hFPB is mediated by a carboxypeptidase. In vitro, this conversion process can be inhibited by the use of o-phenanthroline during blood collection. Unfortunately, it has proven impossible to control the conversion process in vivo. Without knowing how much of the FPB has been metabolized in this way it is simply not possible to determine how much of the FPB is circulating in the blood.

This problem has now been overcome by the generation of an antibody that reacts specifically with or binds specifically to an epitope of fibrinopeptide B, without regard to whether the C-terminal arginine has been removed (and without regard for whether the N-terminal residue is glutamine or pyroglutamic acid). Thus, the antibody permits for the first time the simultaneous detection of both the Bβ1–13 and the Bβ1–14 peptides. Insofar as both forms of FPB are now detectable in one assay, the total amount of circulating FPB is determinable, and an accurate assessment of patient thrombotic status is made possible, once fibrinogen has been removed from a clinical sample by ultrafiltration, ethanol precipitation, or other methods known in the art.

The present invention provides monospecific antibodies that are reactive with or bind with an epitope of fibrinopeptide B, fibrinogen and fragments thereof containing the defining epitope. In particular, the invention provides monospecific antibodies, such as monoclonal antibodies, that are specifically reactive with fibrinopeptide B, des-Arg fibrinopeptide B, and fibrinogen. The invention also provides compositions containing such monospecific antibodies, as well as detectable probes for the detection, localization and purification of fibrinogen and specifically fibrinopeptide B thereof. Methods for preparing such monoclonal antibodies are also provided. Moreover, methods for the preparation of detectable anti-FPB monoclonal antibodies, methods for the use of such antibodies for the detection, localization and purification of fibrinopeptide B and related compounds, and methods for the diagnosis of related disorders, are also provided.

The monospecific antibodies of the invention may exhibit anti-FPB reactivity that is independent of the molecular or cellular context in which fibrinopeptide B occurs. Therefore, the invention includes monospecific antibodies that identify epitopes of fibrinopeptide B, whether as independent molecules or incorporated into a fibrinogen molecule, whether intracellular or extracellular, or whether naturally occurring (native), modified, or synthetic (e.g., recombinant). The monospecific antibodies of the invention may be specifically reactive with a particular form of fibrinopeptide B, or may be reactive with a native or synthetic fragment thereof.

For purposes of more clearly and accurately describing the invention herein, certain terminological conventions have been adopted in the following discussion. These conventions are intended to provide a practical means for enhancing description of the invention, but are not intended to be limiting, and the skilled artisan will appreciate that other and additional, albeit not inconsistent, interpretations can be implied.

An "antibody" in accordance with the present specification is defined broadly as a protein that binds specifically to an epitope. The antibodies are monospecific, preferably monoclonal. Monoclonal antibodies may be produced by methods known in the art. These methods include the immunological method described by Köhler and Milstein (1975) and by Campbell (1985); as well as the recombinant DNA method described by Huse et al. (1989).

As used herein, the term "monospecific antibody" refers to any homogeneous antibody or antigen-binding region thereof that is reactive with, preferably specifically reactive with, a single epitope or antigenic determinant. The term "monospecific antibody" most commonly refers to a monoclonal antibody, also abbreviated "MoAb", as that term is conventionally understood. The term "monospecific antibody" as used herein may, however, refer to homogeneous antibodies that are native, modified, or synthetic, and can include hybrid or chimeric antibodies. The term does not include "polyclonal antibodies" as that term is commonly understood.

The term "antigen-binding region" refers to a naturally occurring, modified, or synthetic fragment of a monospecific antibody of the invention that is reactive with an epitope of fibrinopeptide B or fibrinogen. Such antigen-binding regions include, but are not limited to, Fab, F(ab')$_2$, and Fv fragments.

Functional equivalents of the antibody of the invention further include fragments of antibodies that have the same binding characteristics as, or that have binding characteristics comparable to, those of the whole antibody. Such fragments may contain one or both Fab fragments or the F(ab')$_2$ fragment. Preferably, the antibody fragments contain all six complement determining regions ("CDRs") of the whole antibody, although fragments containing fewer than all of such regions, such as three, four or five CDRs, may also be functional. Fragments may be prepared by methods described by Lamoyi et al. (1983) and by Parham (1983).

Use of the term "monospecific" in connection with the present invention should not be construed to limit the antibody to reactivity with only a single chemical moiety. The antibody has been found to be specifically reactive with an epitope defined by an amino acid sequence SEQ ID NO:1, which is found in a plurality of related protein moieties, including intact fibrinogen as well as fragments thereof, including fibrinopeptide B, des-Arg fibrinopeptide B, and the N-DSK fragment of fibrinogen resulting from cleavage with cyanogen bromide. The term "anti-FPB" refers to the ability of the monospecific antibody of the invention to react specifically with an epitope defined by SEQ ID NO:1, which is characteristic of fibrinogen, fibrinopeptide B, des-Arg fibrinopeptide B, N-DSK, and related peptides.

Accordingly, the antibody of the invention is monospecifically reactive with an epitope defined by an amino acid sequence characteristic of SEQ ID NO:1, and other functionally equivalent sequences, i.e., those amino acid sequences that exhibit similar binding capacities. The antibody is not significantly cross-reactive with moieties lacking the defining epitope.

Among other properties of the antibody of the invention, it is demonstrated herein that the antibody is reactive with peptides containing either SEQ ID NO:2 or SEQ ID NO:3, which differ at their N-termini. This feature implies that the defined epitope is not limited by the character of the N-terminal residue. Accordingly, the antibody of the invention is understood to react specifically with an epitope defined by the amino acid sequence GVNDNEEGFFSA (SEQ ID NO:1). Proteins containing this sequence within their primary structures, and lacking significant steric interference from higher order structures will, therefore, bind with the antibody of the invention. Such proteins may be naturally occurring, such as Fibrin I, or synthetic, e.g., produced by conventional synthetic or recombinant methods such as are known in the art. Homologs of the amino acid sequence characterized by SEQ ID NO:1, and proteins containing the epitope-defining sequence, are also expected to be reactive with the antibody of the invention. However, the antibody exhibits no substantial cross-reaction with moieties lacking this epitope.

The term "fibrinogen" without more is intended to include any type of fibrinogen. Fibrinogen, therefore, refers to monomeric and dimeric fibrinogen molecules having the monomer structure (AαBβγ), as well as molecules having the monomer structure ($A\alpha_E B\beta\gamma$), and other hybrid molecules, whether naturally occurring, modified, or synthetic. The term "fibrinogen" refers generally to fibrinogen from humans, but may include fibrinogen of any species, especially mammalian species. In addition, the term may be specifically limited to a particular species in particular contexts, such as "human fibrinogen."

It is known in the art that monoclonal antibodies are, in general, difficult to produce. For example, it has been estimated that more than 1,000 clones need to be screened to find one or two antibodies that are specific enough and exhibit enough affinity with the antigen to permit use. These difficulties stem from problems such as irreproducibility of an initial positive screen, or failure to obtain subclones in the first cloning. Such problems are commonly related to the deaths of cells, instability in cell lines, low antibody yield in ascites, instability of antibody, etc.

Generally, to be useful as an immunogen, a peptide fragment must contain sufficient amino acid residues to define the epitope of the molecule being detected. If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a cysteine residue on the carrier molecule.

Nonetheless, despite these difficulties, the present invention provides hybridoma cell lines that produce monoclonal antibodies reactive with an epitope of fibrinopeptide B and fibrinogen and fragments thereof containing the epitope. The antibodies produced by these hybridomas are also important aspects of the invention.

The hybridoma technology originally described by K öhler and Milstein (1975) can be used to prepare hybridoma cell lines whose secretory product, monoclonal antibodies, are reactive with an epitope or antigenic determinant of fibrinopeptide B. A general method of preparing these hybridoma cell lines of the invention is described below. Further detail concerning the method is provided in the Examples, which relate the construction a specific hybridoma cell line. Those skilled in the art will recognize that the present invention, including the monoclonal antibodies and hybridoma cell lines described in detail herein, provide a variety of ways to make the hybridomas, and thus the antibodies of the invention. Hybridoma cell lines of the invention can be prepared using fibrinopeptide B or a corresponding immunogenic N-terminal fragment of fibrinogen as immunogenic material for activation of immunologically relevant spleen cells. Generally, a host mammal is inoculated with a peptide or peptide fragment as described above, and then boosted. Spleens are collected from inoculated mammals a few days after the final boost. Antibody-producing spleen cells, are then harvested and immortalized by fusion with mouse myeloma cells. The hybrid cells, called hybridomas, are continuous cell lines resulting from the fuision, which are then selected and screened for reactivity with the peptide. The artisan is referred to Köhler and Milstein ( 1975); Kennett et al. (1980); and Goding (1986) for further details on hybridoma technology. See also Campbell (1985).

The anti-FPB monospecific antibodies described herein are merely illustrative of the invention, and all monospecific antibodies that are specifically reactive with fibrinopeptide B or a fragment thereof, regardless of species of origin or immunoglobulin class or subclass designation, including IgG, IgA, IgM, IgE, and IgD, are included in the scope of this invention. The present invention also provides antigen-binding fragments of the anti-FPB antibodies. The ability to bind to fibrinopeptide B as opposed to non-FPB-containing substances is a general characteristic of monospecific antibodies according to the invention.

As discussed above, monospecific antibodies of the invention can be constructed and isolated by immunization of animals, preparation of hybridomas, and identification of antibodies with a reactivity to fibrinopeptide B and fibrinogen similar to that of the anti-FPB antibodies described. However, the present invention also provides means for identifying monospecific antibodies of the invention that does not require determination of antibody reactivity with a broad number of Bβ-related fragments. Antibodies of the invention can be identified also by immunoprecipitation and competitive binding studies using the antibody produced by the cell lines described herein.

Immunoprecipitations using the anti-FPB monospecific antibody can be used to determine antigenic identity. Confirmation of identity can be obtained by depleting the antigen from testable samples such as plasma samples, using excess amounts of one anti-FPB antibody and observing the inability of another antibody to immunoprecipitate a Bβ-chain fragment from the treated sample. Also, in instances in which the antibodies bind with the same epitope or closely associated epitopes, each antibody will compete with the other(s) for binding to fibrinopeptide B. Competitive binding studies are generally known in the art, and one conventional type is presented in the examples below.

Treatment of antibody preparations with proteolytic enzymes such as papain and pepsin generates antibody fragments, including the Fab and $F(ab')_2$ species, that retain antigen-binding activity. Treatment of the antibodies of the invention with such enzymes can therefore be used to generate fibrinopeptide B antigen-binding fragments of the invention. The preparation of antigen-binding fragments of the antibodies of the invention and their diagnostic and therapeutic usefulness, as well as other applications, suggest themselves to the skilled artisan. Antigen-binding fragments of the anti-FPB antibody are especially useful in therapeutic embodiments of the present invention.

Those skilled in the art will recognize that the antigen-binding region of the antibodies and antibody fragments of the invention is a key feature of the present invention. The anti-FPB hybridoma cells of the invention serve as a preferred source of DNA that encodes such antigen-binding regions of the invention. This DNA, through recombinant DNA technology, can be attached to DNA that encodes any desired amino acid residue sequence to yield a novel "hybrid," or "chimeric," DNA sequence that encodes a hybrid, or chimeric, protein. In such a fashion, chimeric antibodies of the invention, in which one portion of the antibody is ultimately derived from one species and another portion of the antibody is derived from another species, can be obtained. However, the present invention also comprises any chimeric molecule that contains an FPB antigen-binding region.

Antibodies of the present invention can also be labeled by conjugation to any detectable group, such as fluorescent labels, enzyme labels, and radionuclides to identify expression of fibrinogen, or cleavage products including fibrinopeptide B or parts thereof Suitable detectable labels may be selected from among those known in the art, including, but not limited to, radionuclides, enzymes, specific binding pair components, colloidal dye substances, fluorochromes, reducing substances, latexes, digoxigenin, metals, particulates, dansyl lysine, antibodies, protein A, protein G, electron dense materials, chromophores, and the like. Effectively, any suitable label, whether directly or indirectly detectable, may be employed. One skilled in the art will clearly recognize that these labels set forth above are merely illustrative of the different labels that could be utilized in this invention.

Methods for labeling antibodies have been described, for example, by Hunter et al. (1962) and by David et al. (1974). Additional methods for labeling antibodies have been described in U.S. Pat. Nos. 3,940,475 and 3,645,090.

The label may be radioactive, i.e., contain a radionuclide. Some examples of useful radionuclides include $^{32}P$, $^{125}I$, $^{131}I$, $^{111}In$, and $^{3}H$. Use of radionuclides have been described in U.K. patent document No. 2,034,323, U.S. Pat. Nos. 4,358,535, and 4,302,204.

Some examples of non-radioactive labels include enzymes, chromophores, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, and by Rotman (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the antibody probe by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate. Alternatively, labels such as enzymes and chromophoric molecules may be conjugated to the antibodies by means of coupling agents, such as dialdehydes, carbodiimides, dimaleimides, and the like.

The label may also be conjugated to the antibody probe by means of a ligand attached to the probe by a method described above and a receptor for that ligand attached to the label. Any of the known ligand-receptor combinations is suitable. Some suitable ligand-receptor pairs include, for example, biotin-avidin or -streptavidin, and antibody-antigen. The biotin-avidin combination is preferred. Thus, the anti-FPB antibodies of the invention can be derivatized by conjugation to biotin, and used, upon addition of species of avidins that have been rendered detectable by conjugation to fluorescent labels, enzyme labels, radionuclides, electron dense labels, substrates, etc., in a multiplicity of immunochemical and immunohistological applications.

The monospecific antibodies of the invention may also be attached or bound to substrate materials according to methods known to those skilled in the art. Such materials are generally substantially solid and relatively insoluble, imparting stability to physical and chemical disruption of the antibodies, and permitting the antibodies to be arranged in specific spatial distributions. Among substrate materials, materials may be chosen according to the artisan's desired ends, and include materials such as gels, hydrogels, resins, beads, nitrocellulose, nylon filters, microtiter plates, culture flasks, polymeric materials, and the like, without limitation.

The monospecific antibodies of the present invention, whether labeled or unlabeled, can be used in immunological assays to determine the presence of fibrinogen or FPB-associated peptides in tissue samples from human or animal subjects. Biopsy and necropsy samples of subjects, as well as samples from tissue libraries or blood banks, can be evaluated for the presence of fibrinogen and FPB using an anti-FPB antibody of this invention. Moreover, suitable pharmaceutical preparations according to the invention may be employed for in vivo use, such as for the visualization of fibrinogen or FPB-containing substances and structures in a living subject.

Thus, the invention provides a method for binding fibrinopeptide B, fibrinogen or a fragment thereof comprising the amino acid sequence defined by SEQ ID NO:1 by means of the anti-FPB monospecific antibody. Accordingly, fibrinogen and fibrinopeptide B, natural, modified, and synthetic variants thereof, as well as fragments thereof, may be detected and measured by means of monospecific antibodies of the invention.

In the fibrinogen binding method of the invention, the method includes contacting a testable system, in which the presence or absence of fibrinogen is to be determined, with a composition comprising an anti-FPB monospecific antibody or antigen-binding region thereof The method then involves measuring an amount of specific association or binding between an analyte of the testable system and the monospecific antibody. In this method, specific binding of the antibody in the system indicates the presence of the analyte, i.e., fibrinogen or FPB-containing fragments thereof in the system. The testable system may be either in vivo or in vitro, and the method of the invention may be performed in vivo, in vitro, or a combination thereof.

The present invention further provides a method of detecting the presence of fibrinogen or fibrinopeptide B in a sample. The method involves use of a labeled probe that recognizes protein/peptide present in a biological sample such as a blood sample. The probe may be an antibody according to the invention that recognizes FPB-containing analytes present in the sample.

The invention also provides a diagnostic method for the characterization of fibrinogen. In this method, a biological sample such as a body fluid is contacted with an antibody according to the invention to permit the detection of fibrinogen or its degradation products. For example, plasma samples can be assayed using the antibody, before and after ultrafiltration, to allow measurement of peptide concentrations. Such an assay can be used as an index of in vivo thrombin activity. See, e.g., Kudryk et al. (1989b). Other testing methods known in the art can be adapted to use the antibody of the invention.

A typical method involves the differential separation of degradation products, such as separation of the products by gel electrophoresis. The products are then measured by contacting the products with antibodies that are specifically reactive with or specifically associate with one or more domains of fibrinogen. A number of such antibodies are described by Kudryk et al. (1989a). Preferably, such antibodies are specifically reactive with a single degradation product, thereby permitting characterization of the product in relation to other products.

In a preferred embodiment, the detection method employs a monospecific antibody that has been detectably labeled with a marker moiety. In other embodiments, the method may employ a monospecific antibody of the invention that has been bound to a substrate material. In the method, the composition may also include other reagents such as other antibodies that differentially detect other fibrinogen subunits or subtypes. This method can be further adapted for use with at least one other antibody having specificity for alternative fragments, permitting differential analysis or characterization of free FPB or of FPB-containing fragments and other fragments in the same sample. For example, two or more antibodies conjugated to distinct fluorescent labels can be employed as probes in protein separations or other immunometric techniques.

The fibrinogen binding method of the invention includes methods known in the art that employ antibodies to bind target substances specifically. Preferred methods include immunochemical methods, such as enzyme-linked immunosorbent assay (ELISA) methods, immunonephelometry methods, agglutination methods, precipitation methods, immunodiffusion methods, immunoelectrophoresis methods, immunofluorescence methods, and radioimmunoassay methods.

Assays for detecting the presence of proteins with antibodies have been previously described, and follow known formats, such as standard blot and ELISA formats. These formats are normally based on incubating an antibody with a sample suspected of containing the protein and detecting the presence of a complex between the antibody and the protein. The antibody is labeled either before, during, or after the incubation step. The protein is preferably immobilized prior to detection. Immobilization may be accomplished by directly binding the protein to a solid surface, such as a microtiter well, or by binding the protein to immobilized antibodies.

The standard ELISA protocol is exemplary, and is described, for example, by Kennett et al. (1980). Briefly, plates are coated with antigenic protein at a concentration sufficient to bind detectable amounts of the antibody. After incubating the plates with the protein, the plates are blocked with a suitable blocking agent, such as, for example, 10% normal goat serum. The sample, such as patient sera, is added and titered to determine the endpoint. Positive and negative controls are added simultaneously to quantitate the amount of relevant antibody present in the unknown samples. Following incubation, the samples are probed with goat anti-human Ig conjugated to a suitable label, such as an enzyme. The presence of anti-protein antibodies in the sample is indicated by the presence of the label.

In a preferred embodiment, a protein is immobilized on a solid support through an immobilized first antibody specific for the protein. The immobilized first antibody is incubated with a sample suspected of containing the protein. If present, the protein binds to the first antibody.

A second antibody, also specific for the protein, binds to the immobilized protein. The second antibody may be labeled by methods known in the art. Non-immobilized materials are washed away, and the presence of immobilized label indicates the presence of the protein. This and other immunoassays are described in U.S. Pat. No. 4,376,110.

Immunoassays may involve one step or two steps. In a one-step assay, the target molecule, if it is present, is immobilized and incubated with a labeled antibody. The labeled antibody binds to the immobilized target molecule. After washing to remove unbound molecules, the sample is assayed for the presence of the label.

In a two-step assay, immobilized target molecule is incubated with an unlabeled first antibody. The target molecule-antibody complex, if present, is then bound to a second, labeled antibody that is specific for the unlabeled antibody. The sample is washed and assayed for the presence of the label, as described above.

The immunometric assays described above include simultaneous sandwich, forward sandwich, and reverse sandwich immunoassays. These terms are well known to those skilled in the art.

In a forward sandwich immunoassay, a sample is first incubated with a solid phase immunoabsorbent containing antibody against the protein. Incubation is continued for a period of time sufficient to allow the protein in the sample to bind to the immobilized antibody in the solid phase. After the first incubation, the solid phase immunoabsorbent is separated from the incubation mixture and washed to remove excess protein and other interfering substances that also may be present in the sample. Solid phase immunoabsorbent-containing protein bound to the immobilized antibodies is subsequently incubated for a second time with soluble labeled antibody cross-reactive with a different domain on the protein. After the second incubation, another wash is performed to remove the unbound labeled antibody from the solid immunoabsorbent and to remove non-specifically bound labeled antibody. Labeled antibody bound to the solid phase immunoabsorbent is then detected and the amount of labeled antibody detected serves as a direct measure of the amount of antigen present in the original sample. Alternatively, labeled antibody that is not associated with the immunoabsorbent complex can also be detected, in which case the measure is in inverse proportion to the amount of antigen present in the sample. Forward sandwich assays are described, for example, in U.S. Pat. Nos. 3,867,517, 4,012,294, and 4,376,110.

In a reverse sandwich assay, the sample containing the antigen is initially incubated with labeled antibody. A solid-phase immunoabsorbent containing an immobilized antibody that is cross-reactive with a different domain on the antigen is added to the labeled antibody/sample mixture, and a second incubation is carried out. The initial washing step required by a forward sandwich assay is not required, although a wash is performed after the second incubation. Reverse sandwich assays have been described, for example, in U.S. Pat. Nos. 4,098,876 and 4,376,110.

In a simultaneous sandwich assay, the sample, the immunoabsorbent with immobilized antibody, and labeled soluble antibody specific to a different domain on the antigen are incubated simultaneously in one incubation step. The simultaneous assay requires only a single incubation and does not require any washing steps. The use of a simultaneous assay is a very useful technique, providing ease of handling, homogeneity, reproducibility, linearity of the assays, and high precision. See, e.g., U.S. Pat. No. 4,376,110.

In each of the above assays, the sample containing antigen, solid phase immunoabsorbent with immobilized antibody and labeled soluble antibody are incubated under conditions and for a period of time sufficient to allow antigen to bind to the immobilized antibodies and to the soluble antibodies. In general, it is desirable to provide incubation conditions sufficient to bind as much antigen as possible, since this maximizes the binding of labeled antibody to the solid phase, thereby increasing the signal. The specific concentrations of labeled and immobilized antibodies, the temperature and time of incubation, as well as other such assay conditions, can be varied, depending upon various factors including the concentration of antigen in the sample, the nature of the sample and the like. Those skilled in the art will be able to determine operative and optimal assay conditions for each determination by employing routine experimentation.

Many solid phase immunoabsorbents are known and can be used in the present invention. Well-known immunoabsorbents include beads formed from glass, polystyrene, polypropylene, dextran, nylon, and other material; and tubes formed from or coated with such materials, and the like. The immobilized antibodies may be covalently or physically bound to the solid phase immunoabsorbent, by techniques such as covalent bonding via an amide or ester linkage or by absorption.

The invention further includes a method for determining or diagnosing the existence of or probability of thrombogenesis or atherogenesis in a subject. Alternatively, the method includes the detection and localization of fibrotic or atherosclerotic plaques and/or lesions. In this method, an amount of an analyte (e.g., fibrinogen or a fragment thereof comprising SEQ ID NO:1) is measured by means of a composition including an anti-FPB monospecific antibody of the invention. The measured amount of the fibrinogen analyte is compared with an amount of the analyte that is recognized or known to be associated with thrombogenesis or atherogenesis. The method then involves the determination from the measured and standard value(s) of the presence or likelihood of thrombogenesis or atherogenesis in the subject. The method can include measuring or detecting fibrinogen and Bβ1–13 fragments thereof in vivo, such as by imaging or visualizing the location and/or distribution of fibrinogen, and especially fibrinopeptide B, in the body. Alternatively, the method includes obtaining a medical sample from the subject and measuring fibrinogen ex vivo or in vitro. This method preferably involves the differential measurement of at least two epitopes of fibrinogen, including the fibrinopeptide B epitope.

The invention also includes a method for fractionation of fibrinogen or fragments therefor comprising SEQ ID NO:1. Such methods include contacting a medical sample containing fibrinogen or fragments thereof with a composition of the invention that includes an anti-FPB monospecific antibody. Preferably, the method is performed using conditions that are conducive to binding of fibrinogen or fragments thereof with the monospecific antibody. Then the bound fibrinogen or fragments thereof is removed from the sample. The method is represented by chromatography-type methods, both preparative and analytical. Numerous such methods are known in the art and can be selected by the artisan as desired. In this method, the monospecific antibody may be soluble, suspended in fluid phase, or attached to a substantially solid phase, as desired.

The invention further includes a method for purifying fibrinogen or a fragment thereof comprising the amino acid sequence defined by SEQ ID NO:1. For purifying or separating such proteins from other components of biological samples, the method can comprise contacting a sample containing fibrinogen or a Bβ1–13 fragment thereof with a composition comprising a monospecific antibody that binds specifically with the fibrinogen or the fragment, under conditions conducive to binding of the antibody with the fibrinogen or the fragment. Then, the fibrinogen or the fragment are selectively removed from the antibody.

In the method, the monospecific antibody can be soluble, e.g., suspended in a fluid phase, or it can be attached to a solid phase or substrate.

The invention further provides diagnostic and experimental kits that include anti-FPB monospecific antibody, and enable the detection, purification and/or separation of fibrinogen and the various fragments thereof in a specific and reproducible manner. In these kits, the antibodies may be provided with means for binding to detectable marker moieties or substrate surfaces. Alternatively, the kits may include the antibodies already bound to marker moieties or substrates. The kits may further include positive and/or negative control reagents as well as other reagents for adapting the use of the antibodies of the invention to particular experimental and/or diagnostic techniques as desired. The kits may be prepared for in vivo or in vitro use, and may be particularly adapted for performance of any of the methods of the invention, such as ELISA. For example, kits containing antibody bound to multi-well microtiter plates can be manufactured.

EXAMPLES

Throughout the following examples, conventional techniques were used, including in the construction and use of vectors and resultant fusion proteins. Such methods are well known to those of ordinary skill in the art and are described in numerous publications including Sambrook et al. (1989), the complete disclosure of which is incorporated herein by reference. Also conventional methods were employed for the preparation and isolation of the hybridoma and its antibody product. See, e.g., Kennett et al. (1980) and Goding (1986), the complete disclosures of which are incorporated herein by reference.

Example 1

Preparation of Fusion Protein as Immunogen for Monoclonal Antibody Preparation

A fusion protein was prepared for use as an immunogen to prepare a monoclonal antibody. The sense and anti-sense oligonucleotides encoding the first 13 amino acids QGVND-NEEGFFSA (SEQ ID NO:2) of the fibrinogen Bβ chain were synthesized (Chung et al. 1983). After annealing, they formed a double stranded oligonucleotide that was then ligated to form a polymer comprising 9 repeats of Bβ1–3.

A commercially available maltose-binding protein (MBP) vector (pMAL-c2) enables the expression and purification of fusion proteins produced from a cloned gene or open reading frame. The pMAL-c2 vector (6646 base pairs) has an exact deletion of the malE gene of E. coli which encodes the maltose binding protein (the signal sequence). The method uses the strong "tac" promoter and the malE translation initiation signals to give high-level cytoplasmic expression of the cloned gene.

The 9-repeats sequence was inserted into the pMAL-c2 vector downstream from the malE gene, resulting in the expression of a maltose-binding protein fused with the peptide polymer. The MBP fusion protein (designated "MBP/Bβ1–13(9x)") was expressed in E. coli.

Example 2
Generation and Screening of Hybridomas Secreting Monoclonal Antibodies
Immunization and Production of Hybridomas Immunization with the MBP/Bβ1–13(9x) fusion protein was performed in general accordance with the protocol used in preparing the fibrinopeptide A-specific antibody designated MoAb/8C2-5 described by Kudryk et al. (1989b). BALB/c mice (Jackson Lab, Bar Harbor, Me.) were immunized intraperitoneally (i.p.) with the fusion protein (~0.1 mg/animal) mixed with complete Freund's adjuvant. Six subsequent booster injections (i.p.), at two-week intervals, employed the fusion protein mixed with incomplete Freund's adjuvant. After a four-week rest period, the animals were again boosted (i.p.) and, three days following this final boost, the spleen of the animal showing the highest titer was used for fusion. Serum also was collected from this animal prior to sacrifice. Spleen cells were fused with myeloma cells (P3X63Ag8.653) at a ratio of about 4:1 in 1 mL 50% polyethylene glycol (approx. mol. wt. 4000, VWR Scientific, New York, N.Y.) in RPMI 1640 medium (Sigma, St. Louis, Mo.). The remainder of the fusion ("fusion by stirring") procedure was identical to that already described (Harlow et al. 1988).

Testing of Prefusion/Fusion Antisera and Hybridonia Cilliture Media

Antisera were used for titer estimation by enzyme-linked immunosorbent assay (ELISA) and also for immunoblot analysis (see below). In the ELISA procedure, microtiter plates were coated with the following: MBP/Bβ1–13(9x) fusion protein, purified maltose binding protein (MBP), intact human fibrinogen, intact human fibrin II, N-DSK before and after digestion with thrombin, as well as bovine serum albumin (BSA) conjugates prepared with either Bβ1–13 or Bβ1–14. Similar plates were also used in screening hybridoma culture media. Coating of polyvinyl microtiter plates (Costar, Cambridge, Mass.), washing, blocking and antibody detection was similar to that described previously (Kudryk et al. 1983). Polyclonal antisera from animals immunized with the fusion protein bound all but fibrin II and the thrombin-digested N-DSK ("(T)N-DSK"), i.e., (Aα17–51, Bβ15–118, γ1–78)$_2$, ~52 kDa, a non-clottable species missing both FPA and FPB. By contrast, the antibody present in P10 clone culture media (CCF) reacted with only those structures containing SEQ ID NO:1 (i.e., filsion protein, intact fibrinogen and N-DSK, and BSA conjugates of either Bβ1–13 or Bβ1–14).

Production of Ascites, Purification and Isotyping of Antibody

Since antibody levels in ascites are known to be in the 3–15 mg/mL range, hybridoma cell line P10 (see below) was grown in the peritoneal cavity of BALB/c mice using the following protocol. Mice were primed (i.p.) with 0.5 mL Freund's incomplete adjuvant. One day following this stimulation, approximately $10^7$ hybrid cells were injected (i.p.) into animals. Ascites were collected 8–12 days later, filtered on a Millex-PF 0.8 μm filter unit (Millipore Corp, Bedford, Mass.), adjusted to contain 0.1% $NaN_3$, and stored frozen (−70° C.) until needed. Antibody titer in ascites was usually estimated by high-performance liquid chromatography (HPLC) using DEAE or BIO-GEL® HPHT columns. Antibody from ascites was purified by chromatography on BAKERBOND® Abx (J. T. Baker Chemical Co., Phillipsburg, N.J.) as described for ascites prepared by hybridoma cell line 8C2-5 (see Kudryk et al. 1989b and European Patent No. 0 345 811 B 1). The isotype of the purified antibody was determined by conventional ELISA methods. Polyvinyl microtiter plates were coated with antibody at a concentration of about 0.5 μg/mL in $Na_2CO_3$/$NaHCO_3$, pH 9.6 and screening was accomplished using the ScreenType™ kit and procedure obtained from Boehringer Mannheim (Indianapolis, Ind.).

As expected, the vast majority of the isolated clones produced antibodies that were specific for the carrier MBP. However, one antibody was isolated that reacted not only with the fuision protein but also with fibrinogen.

As is detailed in Examples 3 and 4, below, following cleavage at the fusion site of the recombinant protein by bovine plasma coagulation Factor Xa, it was shown that this antibody was unreactive with the MBP carrier. Thus, this antibody was shown to be specifically reactive with the FPB moiety, not only in the synthetic polymeric form but also integrated into fibrinogen. This monospecific antibody and its hybridoma cell line were given the designator "P10." This antibody was characterized as belonging to class IgG1, κ isotype.

Example 3A
Immunoblot Analysis Using P10/HRPO

The P10 antibody was labeled for detectability by attaching horseradish peroxidase (HRPO) to the antibody by conventional means (Kudryk et al. 1999b). An immunoblot was prepared using the detectably labeled P10 antibody to determine other aspects of its binding to fibrinogen-related peptides. To demonstrate specificity, the reactivity of antibody P10 with a panel of samples was contrasted with that obtained with antibody T54-2 (IgG1, κ isotype). The latter antibody is specific for an epitope (Bβ123–127) found in both fibrinogen Bβ-chain (lane 2) and fibrin β-chain (lane 3). The T54-2 antibody also reacts with an N-terminal segment of the fibrinogen Bβ3-chain (Bβ1–190) present in a subpopulation of N-DSK fragments due to incomplete cleavage by CNBr at the Bβ Met118-Tyr119 bond. The T54-2 antibody is described in detail in U.S. patent application Ser. No. 08/900,895, filed Jul. 25, 1997, pending, entitled "Monospecific Antibody Reactive with Matrix Metalloproteinase Cleavage Products of Fibrin(ogen)", the entire disclosure of which is incorporated herein by reference.

Figure 1B:
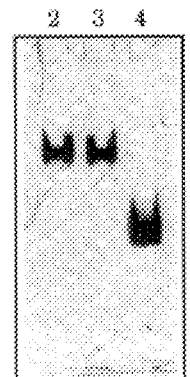
FIG. 1B is a Western blot using a T54-2 antibody-based probe.
Figure 1C:
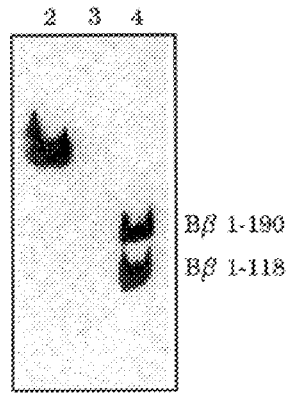
FIG. 1C is a Western blot using a P10-based probe.

FIGS. 1A–1C show electrophoretic separations (SDS-PAGE, 7% gels) of fibrin(ogen)-related samples, after exhaustive reduction with dithiothreitol (DTT) (McDonagh et al. 1972):

Lane 1: protein markers with indicated molecular weights (kDa);
Lane 2: fibrinogen;
Lane 3: XIIIa cross-linked fibrin;
Lane 4: N-DSK.

FIG. 1A is the protein-stained gel. Antibody-reactive bands (FIGS. 1B and 1C) were detected using the chemilurninescent substrate (LUMINOL®) according to manufacturer's specifications (ECL Western blotting detection system, Amersham, Arlington Heights, Ill.).

As shown in FIG. 1C, antibody P10 does not bind fibrin β-chain (lane 3). By contrast, FIG. 1B shows that antibody T54 reacts only with the larger size N-DSK Bβ-chain (Bβ1–190). FIG. 1C also clearly shows that the labeled P10 antibody binds to fibrinogen Bβ chain, but fails to react with the hFPB-free chain of Factor XIIIa cross-linked fibrin. The antibody also binds to two protein bands from reduced N-DSK. The faster moving band is Bβ1–118, and the slower band is Bβ1–190, the latter being present in a small population of N-DSK fragments due to incomplete cleavage by CNBr at the BβMet118-Tyr119 bond. These results are all consistent with monospecific binding of the P 10 antibody with the FPB domain. Moreover, the binding is seen in a number of contexts, including as free FPB, intact fibrinogen, and CNBr digests of fibrinogen, whereas no binding occurs with fibrin that lacks the FPB moiety.

Example 3B
Immunoblot Analysis Using P10 Clone Culture Fluid (CCF)

To further illustrate the unexpected specificity of the P10 antibody as contrasted to that of other antibodies isolated using the method of Example 2, the following samples were electrophoresed (SDS-PAGE, 5→15% gradient gels):
Lane 1: protein markers with indicated molecular weights (kDa) (lane 1);
Lane 2: reduced fibrinogen;
Lane 3: reduced fusion protein (immunogen) prior to cleavage with factor Xa (lane 3).

The results of immunoblot using the P10 and another antibody are shown in FIG. 2. The protein-stained membrane is shown in FIG. 2A. Antibody-bound protein bands (FIGS. 2B and 2C) were detected using horseradish peroxidase-conjugated rabbit anti-mouse immunoglobulin (RAM-HRPO), $H_2O_2$ and 4-chloro-1-naphthol. For comparison, antibody P5/3 (isotype unknown) in P5/3 CCF reacts with the intact immunogen and the "free" maltose binding protein (MBP) but totally fails to react with fibrinogen (FIG. 2B). The P5/3 antibody also fails to react with the fibrinogen Bβ-chain, N-DSK or peptides Bβ1–13 and Bβ1–14 (data not shown). Clearly, the P5/3 antibody is directed to an epitope located on MBP. The P10 antibody, by contrast is clearly reactive with fibrinogen (FIG. 2C).

Example 3C
Immunoblot of Factor Xa Cleavage Products of Fusion Protein

To further demonstrate that the P10 antibody is specific for Bβ1–13-containing peptides as opposed to the MBP carrier, the following samples were electrophoresed (SDS-PAGE, 5→15% gradient gels):
Lane 1: reduced fusion protein (immunogen) prior to cleavage with factor Xa;
Lane 2: reduced fusion protein (immunogen) after cleavage (5 hrs) with factor Xa.

Figure 3A:
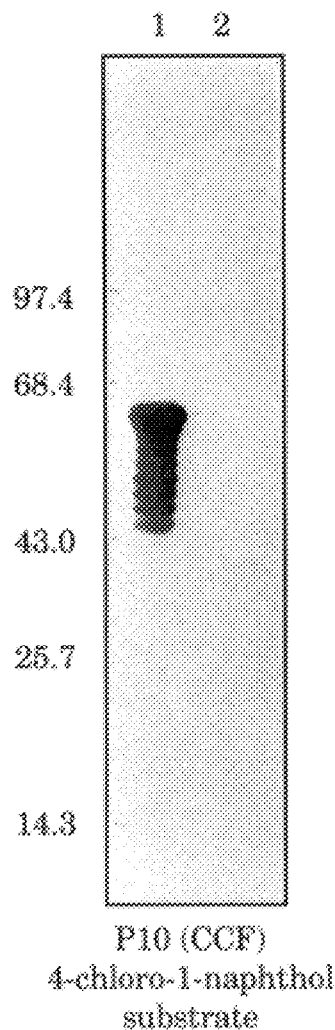
FIG. 3A is an indirect Western blot of a protein separation using P10 antibody as a probe, with 4-chloro-1-naphthol substrate and HRPO-linked to an secondary antibody.
Figure 3B:
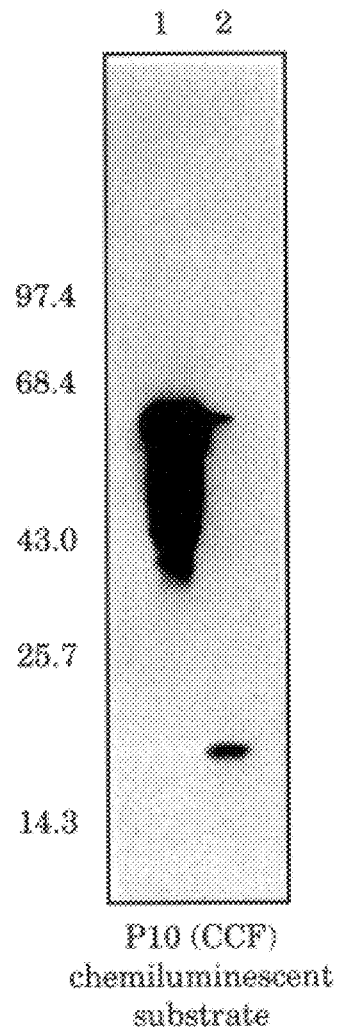
FIG. 3B is an indirect Western blot of a protein separation using P10 antibody as a probe, with a chemiluminescent substrate and HRPO-linked to an secondary antibody

The antibody-bound protein bands in FIG. 3A were detected using RAM-HRPO, $H_2O_2$ and 4-chloro-1-naphthol. The membranes shown in FIG. 3B were treated with the chemiluminescent substrate as in FIG. 1. Following cleavage with bovine plasma coagulation Factor Xa (New England Biolabs, Inc., Beverly, Mass.) as detailed in the manufacturer's instructions, the "free" MBP (~44 kDa) no longer binds antibody P10 whereas the same antibody reacts with the released peptide (lane 2, polymer of Bβ1–13, ~18 kDa).

Figure 4:
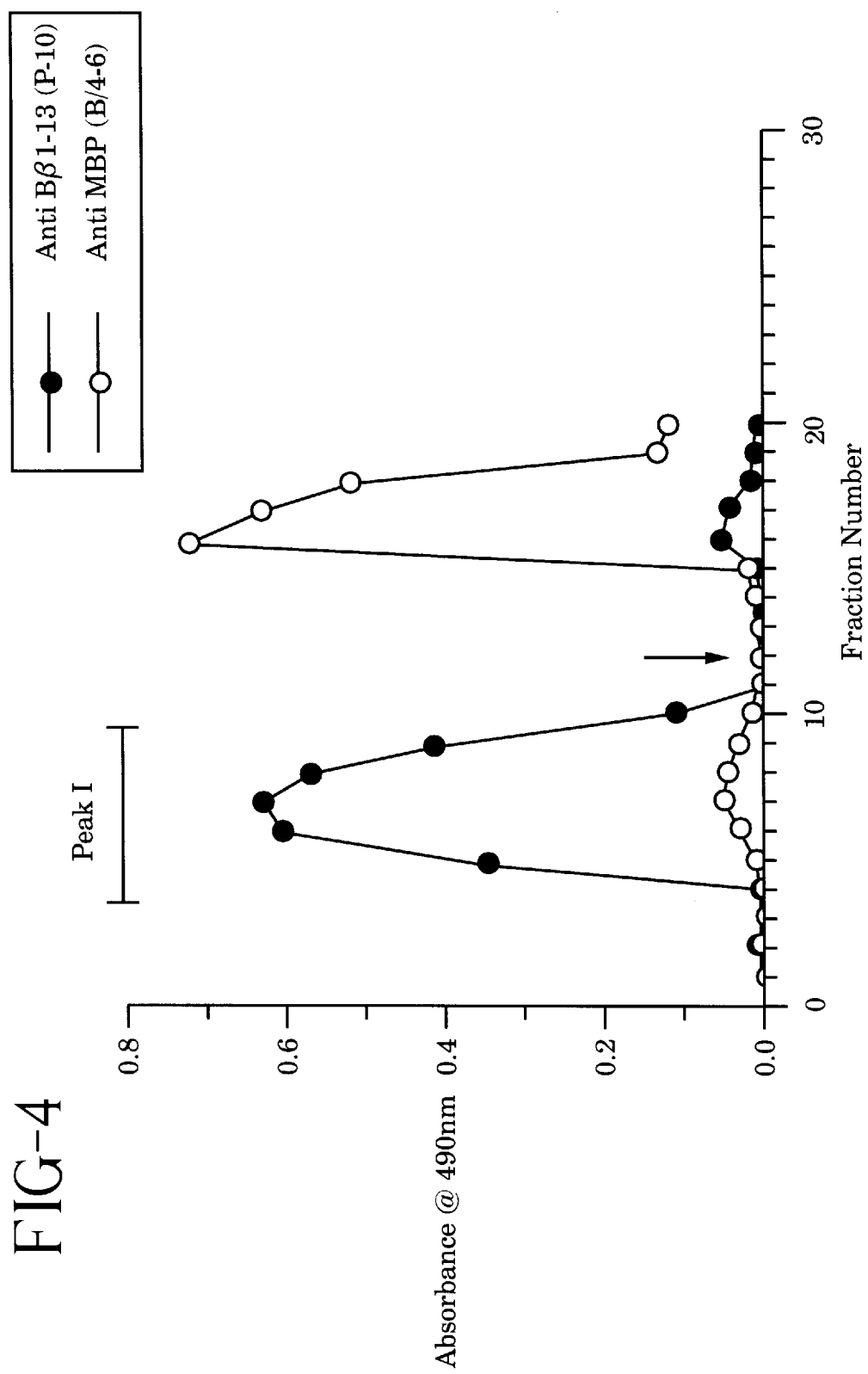
FIG. 4 is a graphic representation of a chromatographic separation of an enzyme cleaved MBP-FPB fusion protein sample, showing reactivity of fractions with the P10 antibody and the B/4-6 antibody.

Example 4
Isolation of Factor Xa Released Peptide (Bβ1–13 Polymer) by Affinity Chromatography The factor Xa digest (prepared as described in Example 3C) was passed over a small amylose column (~3 mL) equilibrated with 20 mM Tris-HCl, pH 7.4, containing 200 mM NaCl, 1 mM EDTA and 1 mM $NaN_3$. FIG. 4 is a graph illustrating the chromatographic separation of two significant peaks. The first peak (Peak I) contained antibody P10-reactive protein. The Peak I fractions were pooled as indicated, desalted, and subjected to sequence analysis (see FIG. 5, below). The second peak (Peak II), containing mostly the antibody P 10 non-reactive MBP, was eluted with the equilibration buffer additionally containing 10 mM maltose. Antibody B/4-6 (isotype unknown) is similar to P5/3 (see FIG. 2) in that it reacts with the intact immunogen and the "free" MBP (i.e., Peak II), but totally fails to react with fibrinogen, its Bβ-chain, N-DSK, or peptides Bβ1–13 and Bβ1–14. Clearly, antibody B/4-6 is also directed to an epitope located on MBP.

Example 5
Structure of Factor Xa-Released Peptide (Bβ1–13 Polymer)

The purified protein of Peak I (described in Example 4) was subjected to amino acid sequence analysis using a pulsed liquid phase sequencer (Model 477A, Applied Biosystems Inc.) with an on-line phenylthiohydantoin (PTH) amino acid analyzer (Model 120A, Applied Biosystems Inc.). The sequence of the initial 15 cycles is given in FIG. 5, with the yield in pmol indicated below each identified residue. The major sequence appears to start with Bβ Gly2. This observation can be explained by assuming the presence of some contaminating enzyme in the factor Xa lot used for release of the fibrinogen-related peptide from the fusion protein. The theoretical structure of the Xa-cleaved, amylose resin non-adsorbed, peptide is given at the top of FIG. 5. The structure of this peptide should start with the first four vector-derived residues (ISEF). As shown in FIG. 5, a peptide with this sequence was identified, but it was not the major peptide.

Example 6
Immunoaffinity Chromatography Using Antibody P10

Matrix metalloproteinases (MMPs) have the capacity to degrade a number of proteins and proteoglycans that constitute basement membranes and the extracellular matrix of connective tissue. Two recent studies have shown the presence of MMPs in atherosclerotic plaques. We and others have previously shown that such plaques also contain large amounts of fibrinogen-related antigen. Our present hypothesis is that MMPs might play a role in the degradation of fibrin(ogen) in atheromas. As already described in our recently published study (Bini et al. 1996), digestion of fibrinogen (Fg) or XIIIa cross-linked fibrin (XL-Fb) by matrix metalloproteinase 3 (Stromelysin 1, MMP-3) results in loss of reactivity with MoAb/4A5 (anti-γ397–411). This is in contrast to plasmin where loss of this epitope from either substrate occurs only if digests with plasmin are carried out in a $Ca^{2+}$-free environment. In more recent as yet unpublished studies, we have shown several other major immunochemical differences in digests by various MMPs compared with those generated by plasmin. At present we do not know the fate of the Bβ1–13/Bβ1–14 segment of fibrinogen during its cleavage with MMP-3 or any other enzyme of this family.

One application of the P 10 antibody is as an immunoaffinity matrix for isolating and subsequently characterizing the molecular nature of MMP-generated degradation products. It is possible that different size peptides containing the Bβ1–13/Bβ1–14 segment of fibrinogen are released by different MMPs and that identifying such peptides in clinical samples could provide information on the nature and extent of MMP activity in vivo. It has been known for sometime that Bβ1–42 is the principal species released from fibrinogen or fibrin I by plasmin action (Hurlet-Jensen et al. 1983). Peptide Bβ1–42 reacts completely with antibody P10 and, therefore, would bind to affinity columns prepared with this antibody.

Accordingly, the following demonstration of this principle was performed. The antibody was purified from ascitic fluid by methods described previously (see Kudryk et al. 1989b and European Patent No. 0 345 811 B1) and was later covalently coupled to an AminoLink™ column (2 mL) according to instructions provided by the manufacturer (Pierce, Rockford, Ill.). A mixture of peptides found in a fibrin clot supernatant was applied to the P10 antibody column that had been previously equilibrated with buffer A-3 (40 mM Tris-HCl, pH 7.5, 110 mM NaCl, 0.1% $NaN_3$).

The fractions collected from the P10 column were divided into P 10-non-adsorbed fraction and a P10 adsorbed fraction, each of which was further analyzed by high performance liquid chromatography (HPLC) on a Vydac 214TP butyl $C_4$ reverse phase column (10×250 mm) to determine content.

As a control, the mixture of peptides applied to the P 10 column was also analyzed by HPLC. Three principle peaks were identified (FIG. 6A), which were designated in order of elution: Peaks I, II, and III.

Figure 6A:
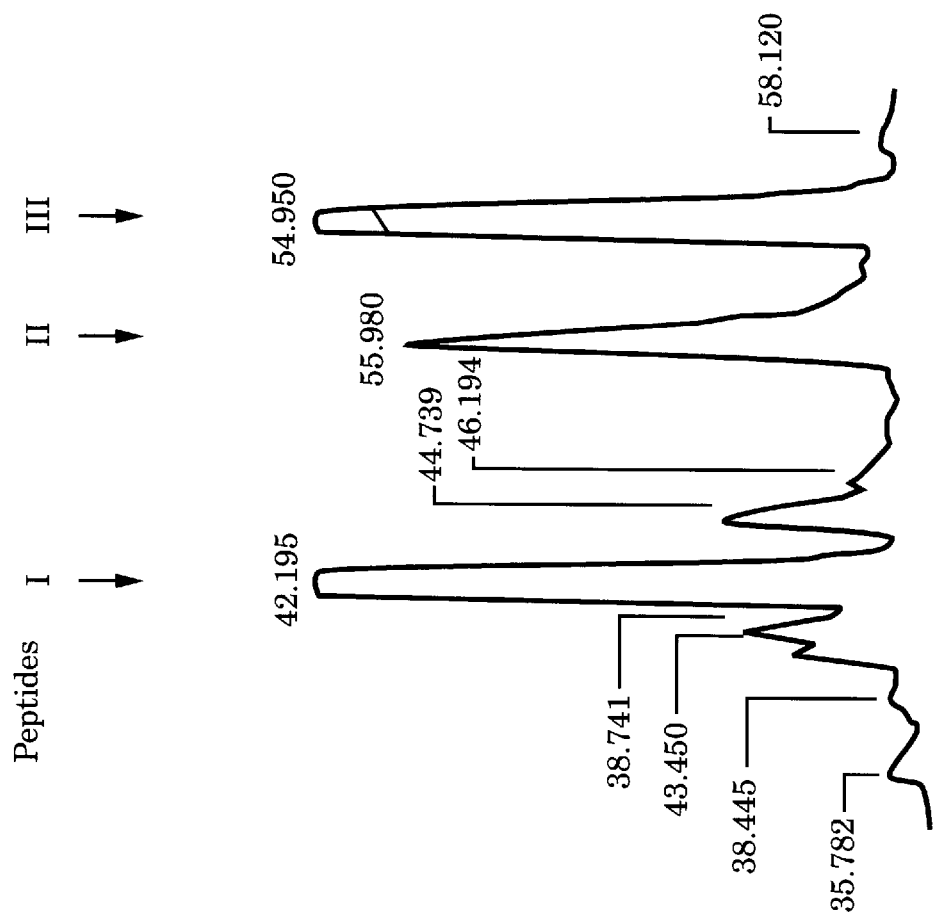
FIG. 6A is an HPLC chromatogram showing a separation of mixed fibrinogen-related peptides prior to immunoaffinity separation using the P10 antibody.
Figure 6B:
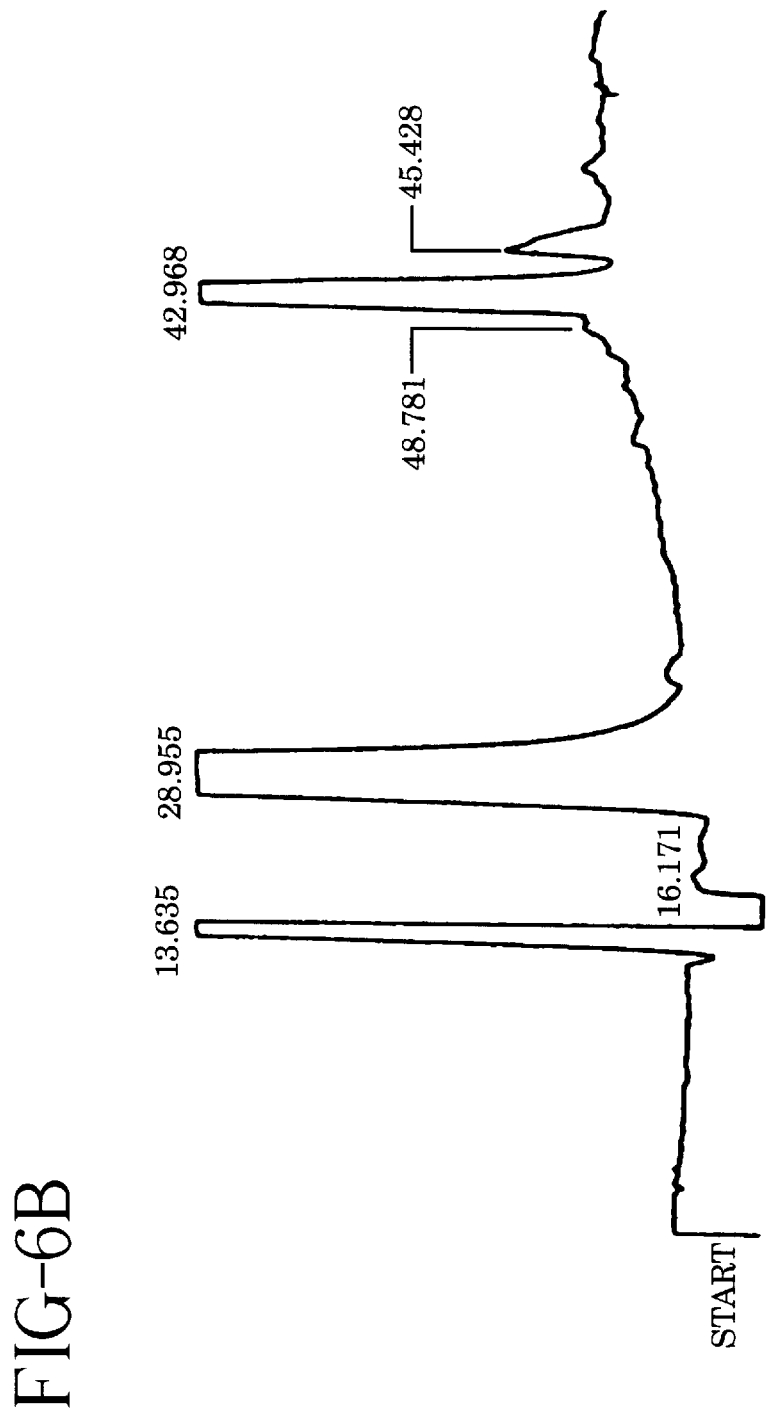
FIG. 6B is an HPLC chromatogram showing a separation of P10 non-adsorbed fraction collected from a P10 immunoaffinity column separation of mixed fibrinogen-related peptides.

FIG. 6B is an HPLC chromatogram of the P 10 non-adsorbed fraction, containing a peak, i.e., the large peak at the right side of the chromatogram, corresponding to Peptide I of the mixed material. This peptide was identified by sequence analysis as human fibrinopeptide A (data not shown). The other major peaks in FIG. 6A are non-peptide buffer salts.

Figure 6C:
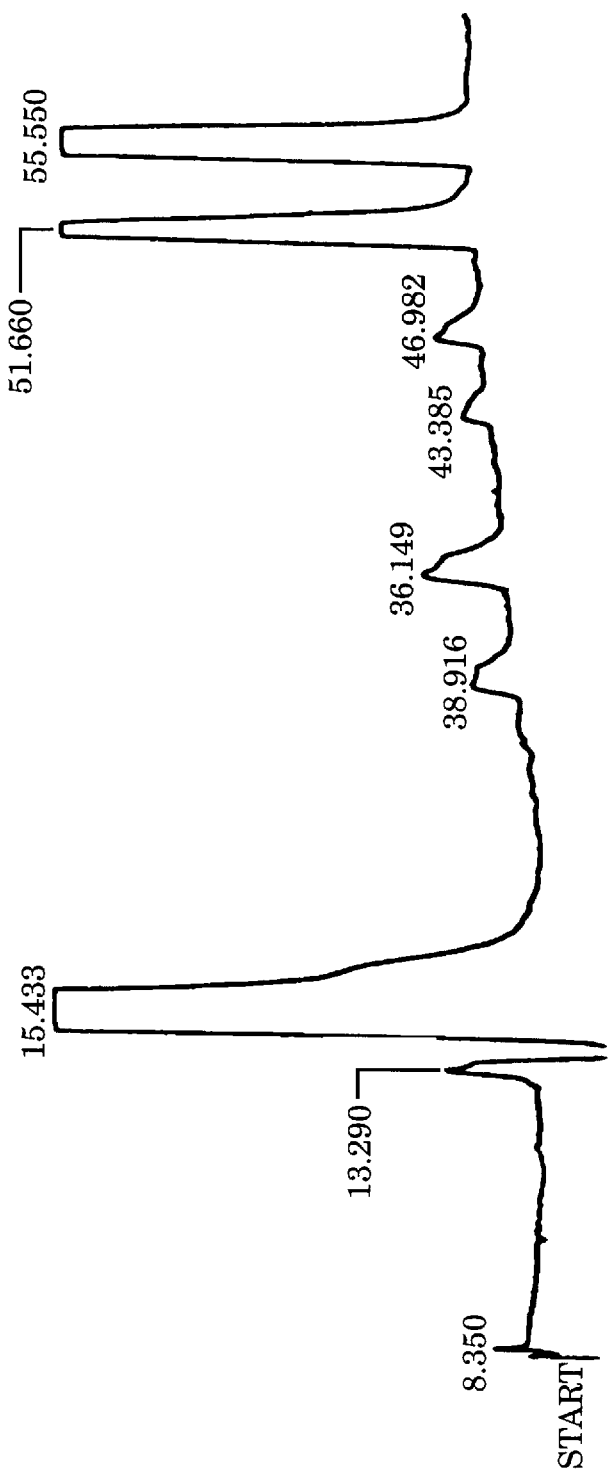
FIG. 6C is an HPLC chromatogram showing a separation of P10 adsorbed fraction collected from a P10 immunoaffinity column separation of mixed fibrinogen-related peptides.

FIG. 6C is a chromatogram showing the HPLC separation of the PI10-adsorbed peptides, eluted from the antibody column with equilibration buffer additionally containing 3M NaSCN. The two peaks at the far right of the graph correspond to Peaks I and II of the mixed peptides separation. Amino acid analysis confirmed that Peptide II ($R_t$~51.7 min) corresponds to FPB, and that Peptide III ($R_t$55.6 min) is the des-Arg species (data not shown).

These data clearly demonstrate that FPB-containing peptides can be effectively purified from a mixture of fibrinogen-derived peptides by immunoaffinity chromatography using the monospecific antibody of the invention.

Example 7A
ELISA-Determined Standard Dose-Response Curves of Reactivity of P10/HRPO A competition ELISA was performed according to conventional methods (see, e.g., Kudryk et al. 1989b), to determine the comparative affinity of the P10 antibody for fibrinogen, Bβ1–13 (des-Arg hFPB), and Bβ1–14 (hFPB). Specifically, plates were coated with intact fibrinogen. Inhibition was determined using the equation: $I=(A/A_o)\times 100$, where A is absorbance in the presence of a competitor, and $A_o$ is the absorbance in control wells (buffer with no competitor). The dose-response reactivity data were linearized by means of logit transforms (Rodbard et al. 1969). Since fibrinogen contains 2 mols FPB/mol, fibrinogen inhibitor concentration was calculated on 170 kDa.

Figure 7:
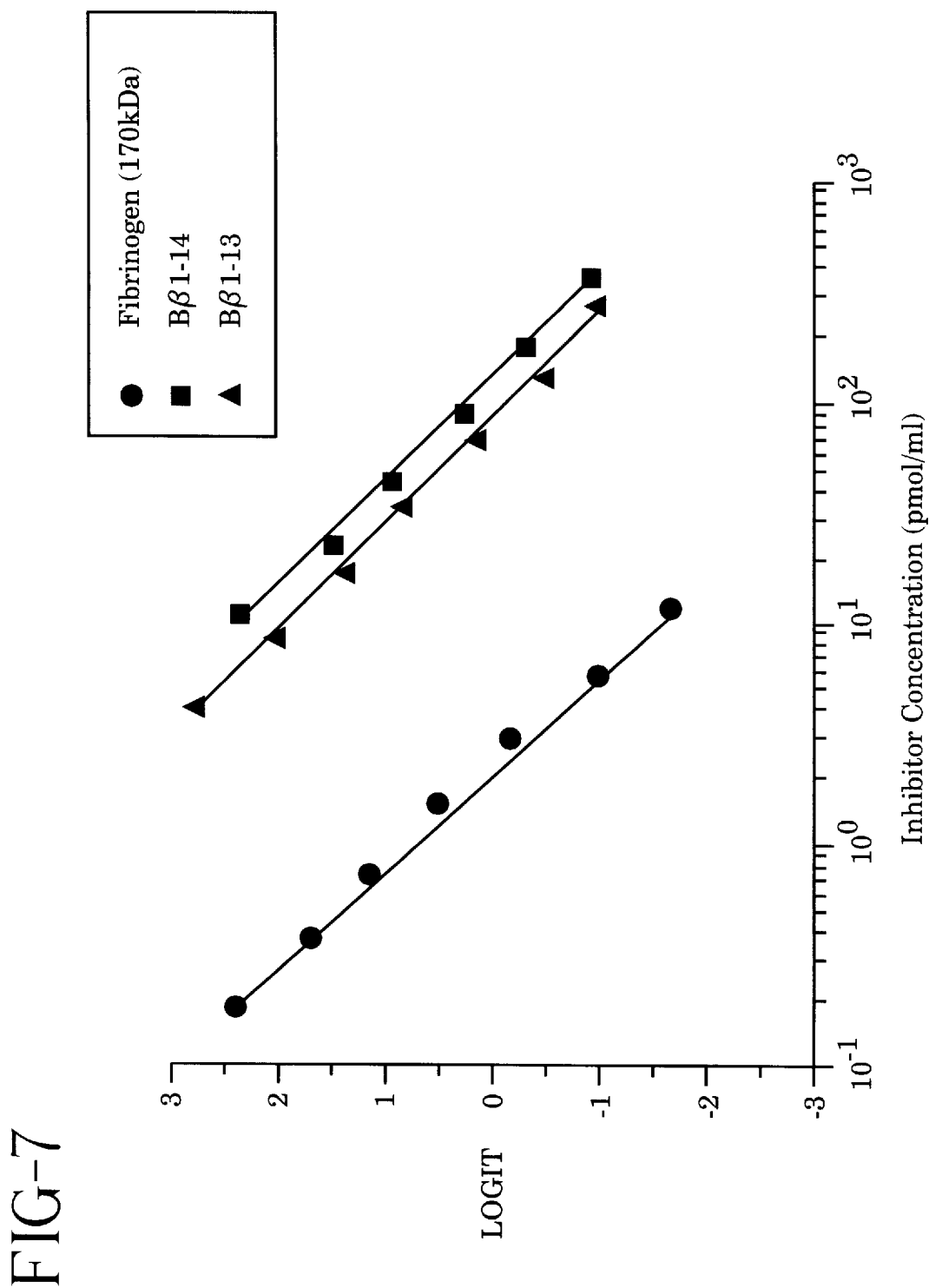
FIG. 7 is a graph illustrating a competition ELISA using the P10 antibody.

The results of this assay are presented graphically in FIG. 7. FIG. 7 shows that the P10 antibody is substantially more reactive with intact fibrinogen than with either of the Bβ peptides. However, FIG. 7 also shows that the P10 antibody does not discriminate between the two forms of hFPB. Therefore, the P10 antibody is well suited for use in immunoassays to detect total hFPB peptide content in a biological sample.

It should be understood that this assay will not reflect a true picture of the FPB content when performed directly on patient plasma samples, due to the strong reactivity of the antibody with fibrinogen. This strong reactivity with fibrinogen would prevent direct assessment of the actual content of FPB peptides. Also, an hFPB-containing peptide, Bβ1–42, is generated at a variable rate in plasma in vitro. Moreover, neither addition of most common inhibitors (e.g., TRASYLOL® (aprotinin), heparin, EDTA, ε-aminocaproic acid (EACA), soybean trypsin inhibitor, p-aminobenzamidine, or a combination of heparin, TRASYLOL®, EACA and benzamidine), nor storage of plasma below −70° C., prevents the generation of the Bβ1–42 peptide (Nossel et al. 1979). Therefore, it is advisable to process patient plasma to remove fibrinogen prior to assay for fibrinogen-derived peptides.

For example, fibrinogen can be removed from plasma by precipitation with ethanol (Kudryk et al. 1982). This procedure does not guarantee total removal but peptides such as Bβ1–13 or FPB are almost quantitatively retained in the ethanol supernatant. Generally, the ethanol supernatant is further processed by ultrafiltration (e.g., using a cell with a 10 kDa cutoff). In this way, small amounts of fibrinogen not precipitated by ethanol are removed and peptides of low molecular weight, such as Bβ1–13 or FPB, are recovered in the ultrafiltrate. Alternatively, plasma samples may be ultrafiltered directly but filtration is slow and there is always the possibility that peptides such as Bβ1–13 or FPB can be cleaved during this procedure.

Example 7B
ELISA-Determined Standard Dose-Response Curves of Reactivity of P 10

Figure 8:
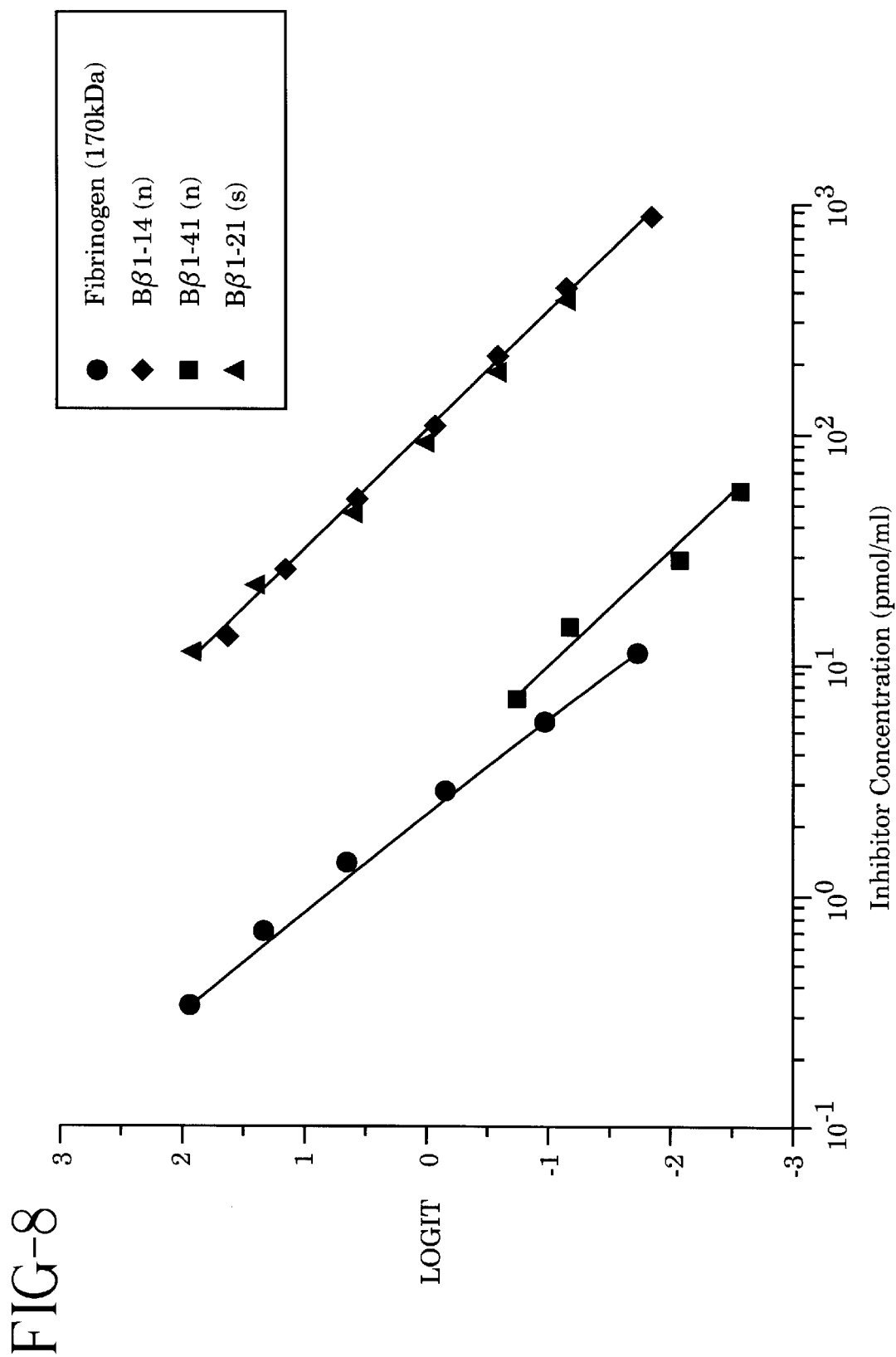
FIG. 8 is a graph illustrating a competition ELISA using the P10 antibody.

A competition ELISA was performed, generally as described in Example 7A, to determine the reactivity of another group of inhibitors and the P10 antibody. The results are illustrated in FIG. 8. Peptide Bβ1–14(n) shown in FIG. 8 corresponds to the fragment identified as Peptide II in Example 6 (see FIGS. 6A–6C). Peptide Bβ1–21 was prepared on a Biosearch Model 9600 peptide synthesizer. Peptide Bβ1–41 was isolated from a factor Xa digest of MBP/Bβ1–41 fusion protein. The latter was made using a vector and protocol similar to that described above for preparation of the antibody P10 immunogen (Example 1).

Example 7C
ELISA-Determined Standard Dose-Response Curves of Reactivity of P10

Another competition ELISA was performed, generally as described in Example 7A, to determine the reactivity of another group of inhibitors and the P10 antibody. The results are illustrated in FIG. 9, N-DSK used in this experiment was isolated from an HPLC fraction of CNBr-cleaved fibrinogen by P10 affinity chromatography. (T)N-DSK was generated from N-DSK by digestion with thrombin. This thrombin-digested fragment differs from N-DSK in that both fibrinopeptides A and B have been cleaved. In contrast to fibrin, (T)N-DSK is a completely non-clottable fragment that can also be obtained directly from fibrin by cleavage with CNBr. (The observed minor binding of (T)N-DSK is insubstantial, especially when contrasted against binding to the other substrates, and may be due to incomplete digestion.)

Example 8
Immunohistochemical Application of an Anti-FPB Antibody

The P10 antibody is labeled with a fluorescent chemical tag, fluorescein isothiocyanate. A tissue sample is collected and mounted for microscopic analysis, and stained using the labeled P10 antibody. Under microscopic observation, using an appropriate light source, the labeled antibody is observed to bind specifically with fibrinogen- or Bβ1–13-containing regions or structures in the tissue, thereby enabling ready differentiation of those regions or structures from other regions or structures, including those stained with other dyes. In particular, the fluorescent-labeled antibody enables the immunohistochemical detection of fibrinogen-related antigens in vascular and extravascular spaces.

BIOLOGICAL DEPOSIT

The invention as claimed is enabled in accordance with the specification and readily available references and starting materials. Nevertheless, Applicants shall deposit with the American Type Culture Collection, Manassas Va., USA (ATCC) the hybridoma cell line described hereinabove.

The P10 hybridoma cell line described hereinabove was deposited with ATCC on 10 Sep. 1997 and assigned ATCC Accession No. HB-12398.

This deposit shall be made under the provisions of the Budapest Treaty on the International Recognition of the Deposit of Microorganisms for the Purposes of Patent Procedure and the regulations thereunder (Budapest Treaty). This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

The following publications having been mentioned in the foregoing specification, and are incorporated herein by reference for all that they disclose:

Bini A, Fenoglio J J, J Sobel, Owen J, Fejgl M, and Kaplan K L, "Immunochemical characterization of fibrinogen, fibrin I, and fibrin II in human thrombi and atherosclerotic lesions," *Blood* 69:1038–1045 (1987).

Bini A and Kudryk B J, "Fibrin and its derivatives in the normal and diseased vessel wall," *Ann NY Acad Sci* 667:112–126 (1992).

Bini A, Itoh Y, Kudryk B J, and Nagase H, "Degradation of cross-linked fibrin by matrix metalloproteinase 3 (stromelysin 1): Hydrolysis of γGly404-Ala405 peptide bond," *Biochemistry* 35(40):13056–13063 (1996).

Blombäck B, Blombäck M, Henschen A, Hessel B, Iwanaga S, and Woods K R, "N-terminal disulphide knot of human fibrinogen," *Nature* 218:130–134 (1968).

Blombäck B, "Fibrinogen and fibrin formation and its role in fibrinolysis," pp. 225–279, in *Biotechnology of Blood*, Goldstein J, ed., Butterworth-Heinemann, Boston (1991).

Campbell, "Monoclonal antibody technology, the production and characterization of rodent and human hybridomas" in Burdon et al., eds, *Laboratory Techniques in Biochemistry and Molecular Biology*, Volume 13, Elsevier Science Publishers, Amsterdam (1985).

Cheresh D A, Berliner S A, Vicente V, and Ruggeri Z M, "Recognition of distinct adhesive sites on fibrinogen by related integrins on platelets and endothelial cells," *Cell* 58:945–953 (1989).

Chung D W, Que B G, Rixon M W, Mace M Jr, Davie E W, "Characterization of complementary deoxyribonucleic acid and genomic deoxyribonucleic acid for the β chain of human fibrinogen," *Biochemistry* 22(13):3244–3250 (1983).

Chung D W, Harris J E, and Davie E W, "Nucleotide sequences of the three genes coding for human fibrinogen," *Adv Exp Med Biol* 281:39–48 (1991).

David G S and Reisfeld R A, "Protein iodination with solid state lactoperoxidase," *Biochemistry* 13(5):1014–1021 (1974).

Doolittle R F, Watt K W K, Cottrell BA, Strong D D, and Riley M, "The amino acid sequence of the alpha-chain of human fibrinogen," *Nature* 280:464–468 (1979).

Doolittle R F, "Fibrinogen and fibrin," *Annu Rev Biochem* 53:195–229 (1984).

Doolittle R F, "Fibrinogen and fibrin," in Bloom A L, and D P Thomas, eds., *Hemostasis and Thrombosis*, Churchill Livingston, Edinburgh, New York (1987).

Dvorak H F, Nagy J A, Berse B, Brown L F, Yeo K-T, Yeo T-K, Dvorak A M, Van de Water L, Sioussat T M, and Senger D R, "Vascular permeability factor, fibrin, and the pathogenesis of tumor stroma formation," *Ann NY Acad Sci* 667:101–111 (1992).

Ernst E, "Plasma fibrinogen—An independent cardiovascular risk factor," *J Internal Med* 227:365–372 (1990).

Ernst E and Resch K L, "Fibrinogen as a cardiovascular risk factor: A meta-analysis and review of the literature," *Ann Intern Med* 118:956–963 (1993).

Farrell D H, Thiagarajan P, Chung D W, and Davie E W, "Role of fibrinogen alpha and gamma chain sites in platelet aggregation," *Proc Natl Acad Sci USA* 89:10729–10732 (1992).

Felding-Habermann B, Ruggeri Z M, and Cheresh D A, "Distinct biological consequences of integrin alpha v beta 3-mediated melanoma cell adhesion to fibrinogen and its plasmic fragments," *J Biol Chem* 267:5070–5077 (1992).

Fu Y, Weissbach L, Plant P W, Oddoux C, Cao Y, Liang T J, Roy S N, Redman C M, and Grieninger G, "Carboxy-terminal-extended variant of the human fibrinogen α subunit: a novel exon conferring marked homology to β and γ subunits," *Biochemistry* 31:11968–11972 (1992).

Fu Y and Grieninger G, "Fib$_{420}$: A normal human variant of fibrinogen with two extended α chains," *Proc Natl Acad Sci USA* 91:2625–28 (1994).

Goding J W, in *Monoclonal Antibodies: Principles and Practice*, Academic Press, New York, N.Y. (1986).

Gonda S R and Shainoff J R, "Adsorptive endocytosis of fibrin monomer by macrophages: Evidence of a receptor for the amino terminus of the fibrin alpha chain," *Proc Natl Acad Sci USA* 79:4565–4569 (1982).

Harlow E and Lane D, *Antibodies: A Laboratory Manual*, Cold Spring Harbor Laboratory Press, Cold Spring Harbor, N.Y. (1988).

Henschen A and Lottspeich F, "Amino Acid sequence of human fibrin, preliminary note on the completion of the beta-chain sequence," *Hoppe-Seyler's Z. Physiol Chem* 358:1643–1646 (1977).

Henschen A, Lottspeich F, and Hessel B, "Amino acid sequence of human fibrin, preliminary note on the completion of the intermediate part of the alpha-chain sequence," *Hoppe-Seyler's Z Physiol Chem* 360:1951–1956 (1979).

Hunter W M and Greenwood F C, "Preparation of Iodine-131 labelled human growth hormone of high specific activity," *Nature* 144:495–496 (1962).

Hurlet-Jensen A, Koehn J A, and Nossel H L, "The release of Bβ1–42 from fibrinogen and fibrin by plasmin," *Thromb Res* 29:609–617 (1983).

Huse W D, Sastry L, Iverson, S A, Kang A S, Alting-Mees M, Burton D R, Benkovic S J, and Lerner R A, "Generation of a large combinatorial library of the immunoglobulin repertoire in phage lambda," *Science* 246:1275–1281 (1989).

Hynes R O, "Integrins: Versatility, modulation, and signaling in cell adhesion," *Cell* 69:11–25 (1992).

Kant J A, Fornace A J Jr, Saxe D, Simon M I, McBride O W, and Crabtree G R, "Evolution and organization of the fibrinogen locus on chromosome 4: Gene duplication accompanied by transposition and inversion," *Proc Natl Acad Sci USA* 82:2344–2348 (1985).

Kennett R H, McKearn T J, and Bechtol K B, eds., *Monoclonal Antibodies. Hybridomas: A New Dimension in Biological Analyses*, Plenum Press, New York (1980).

Kloczewiak M, Timmons S, Lukas T J, and Hawiger J, "Platelet receptor recognition site on human fibrinogen. Synthesis and structure-function relationship of peptides corresponding to the carboxy-terminal segment of the gamma chain," *Biochemistry* 23:1767–1774 (1984).

Köhler G and Milstein C, "Continuous cultures of fused cells secreting antibody of predefined specificity," *Nature* 256:495–497 (1975).

Kudryk B, Robinson D, Netre C, Hessel B, Blombäck M, and Blombäck B, "Measurement in human blood of fibrinogen/fibrin fragments containing the Bβ15–42 sequence," *Thromb Res* 25:277–291 (1982).

Kudryk B, Rohoza A, Ahadi M, Chin J, and Wiebe M E, "A monoclonal antibody with ability to distinguish between $NH_2$-terminal fragments derived from fibrinogen and fibrin," *Mol Immunol* 20:1191–1200 (1983).

Kudryk B J, Grossman Z D, McAfee J G, and Rosebrough S F, "Monoclonal antibodies as probes for fibrin(ogen) proteolysis," Chapter 19 in *Monoclonal Anlibodies in Immunoscintigraphy*, Chatal J-F, ed., CRC Press, Boca Raton (1989a).

Kudryk B, Gidlund M, Rohoza A, Ahadi M, Coiffe D, and Weitz J I, "Use of a synthetic homologue of human fibrinopeptide A for production of a monoclonal antibody specific for the free peptide," *Blood* 74(3): 1036–1044 (1989b).

Lamoyi E and Nisonoff A, "Preparation of F(ab')$_2$ fragments from mouse IgG of various subclasses," *J Immunol Meth* 56:235–243 (1983).

Loike J D, Sodeik B, Cao Y, Leucona S, Weitz J I, Detmers P A, Wright S D, and Silverstein S C, "CD11c/CD 18 on neutrophils recognizes a domain at the N terminus of the A-alpha chain of fibrinogen," *Proc Natl Acad Sci USA* 88: 1044–1048 (1991).

Lottspeich F and Henschen A, "Amino acid sequence of human fibrin. Preliminary note on the completion of the gamma-chain sequence," *Hoppe-Seyler 's Z Physiol Chem* 358:935–938 (1977).

McDonagh J, Messel H, McDonagh R P Jr, Murano G, and Blombäck B, "Molecular weight analysis of fibrinogen and fibrin chains by an improved sodium dodecyl sulfate gel electrophoresis method," *Biochim Biophys Acta* 257:135–42 (1972).

Nossel H L and Kaplan K L, "Simultaneous measurement of thrombin and plasmin proteolysis of fibrinogen and of platelet release," pp. 97–110 in *The Chemistry and Physiology of the Human Plasma Proteins*, Bing D, ed., Pergamon Press, New York (1979).

Parham P, "On the fragmentation of monoclonal IgG1, IgG2a, IgG2b from BALB/c mice," *J Immunol* 131(6):2895–2902 (1983).

Ribes J A, Ni F, Wagner D D, and Francis C W, "Mediation of fibrin-induced release of von Willebrand factor from cultured endothelial cells by the fibrin beta chain," *J Clin Invest* 84:435–442 (1989).

Rodbard D, Bridson W, and Rayford P L, "Rapid calculation of radioimmunoassay results," *J Lab & Clin Med* 74(5): 770–781 (1969).

Rotman, *Proc Natl Acad Sci USA* 47:1981–1991 (1961).

Sambrook J, Fritsch E F, and Maniatis T, *Molecular Cloning: A Laboratory Manual*, 2d ed., Cold Spring Harbor Laboratory Press, Cold Spring Harbor, N.Y. (1989).

Sehgal P B, Grieninger G, and Tosato G, eds., "Regulation of the acute phase and immune responses: Interleukin-6, "*Ann NY Acad Sci* 557:1–583 (1989).

Valenzuela R, Shainoff J R, DiBello P M, Urbanic D A, Anderson J M, Matsueda G R, and Kudryk B J, "Immunoelectrophoretic and immunohistochemical characterizations of fibrinogen derivatives in atherosclerotic aortic intimas and vascular prosthesis pseudo-intimas," *Amer J Pathol* 141:861–880 (1992).

---

What is claimed is:

1. A continuous cell line, identified as P10 and deposited as ATCC Accession No. HB-12398, that produces a monoclonal antibody that binds specifically with an epitope defined by amino acid sequence SEQ ID NO:1.

2. The monospecific antibody produced by hybridoma cell line p10 deposited as ATCC Accession No. HB-12398, or an antigen-binding fragment thereof, that binds specifically with an epitope defined by amino acid sequence SEQ ID NO:1.

3. The monospecific antibody or fragment thereof according to claim 2, that binds specifically with the epitope as present in fibrinogen, fibrinopeptide B, or des-Arg fibrinopeptide B.

4. The monospecific antibody or fragment thereof according to claim 2, wherein the antibody or fragment thereof is detectably labeled by conjugation to a detectable moiety.

5. The monospecific antibody or fragment thereof according to claim 4, wherein the detectable moiety is selected from the group consisting of radionuclides, enzymes, specific binding pair components, colloidal dye substances, fluorochromes, reducing substances, latexes, digoxigenin, metals, particulates, dansyl lysine, antibodies, protein A, protein G, electron dense materials, and chromophores.

6. The monospecific antibody or fragment thereof according to claim 2, wherein the antibody or fragment thereof is attached to a substrate.

7. The monospecific antibody or fragment thereof according to claim 6, wherein the substrate includes a component selected from the group consisting of gels, hydrogels, resins, beads, nitrocellulose, nylon filters, microtiter plates, culture flasks, and polymeric materials.

8. The monospecific antibody or fragment thereof according to claim 2, wherein the fragment thereof is an Fab, F(ab')$_2$, or Fv fragment of the monospecific antibody produced by the P10 hybridoma.

9. The composition for binding fibrinogen or fibrinopeptide B, comprising a monospecific antibody produced by hybridoma cell line P10 deposited as ATCC Accession No. HB-12398, or an antigen-binding fragment thereof, that binds specifically with an epitope defined by amino acid sequence SEQ ID NO:1.

10. The composition according to claim 9, wherein the monospecific antibody or fragment thereof binds specifically with the epitope as present in fibrinogen, fibrinopeptide B, or des-Arg fibrinopeptide B.

11. The composition according to claim 9, wherein the antibody or fragment thereof is detectably labeled by conjugation to a detectable moiety.

12. A composition according to claim 11, wherein the detectable moiety is selected from the group consisting of radionuclides, enzymes, specific binding pair components, colloidal dye substances, fluorochromes, reducing substances, latexes, digoxigenin, metals, particulates, dansyl lysine, antibodies, protein A, protein G, electron dense materials, and chromophores.

13. A composition according to claim 9, wherein the antibody or fragment thereof is attached to a substrate.

14. A composition according to claim 13, wherein the substrate includes a component selected from the group consisting of gels, hydrogels, resins, beads, nitrocellulose, nylon filters, microtiter plates, culture flasks, and polymeric materials.

15. The composition according to claim 9, wherein the fragment thereof is an Fab, F(ab')$_2$, or Fv fragment of the monospecific antibody produced by the P10 hybridoma.

16. The composition according to claim 9, wherein the composition further comprises a second antibody, wherein the second antibody binds specifically with fibrinogen or a subunit or fragment thereof.

17. The method of detecting fibrinogen or a fragment thereof comprising amino acid sequence SEQ ID NO:1 as antigen in a biological sample, the method comprising:

contacting the biological sample with a composition comprising a monospecific antibody produced by hybridoma cell line P10 deposited as ATCC Accession NO. HB-12398, or an antigen-binding fragment thereof, that binds specifically with an epitope defined by amino acid sequence SEQ ID NO:1, and measuring a level of specific binding of the antibody, or fragment thereof, to any of said antigen present in the sample, wherein the level of specific binding is indicative of presence or amount of said fibrinogen or fragment thereof comprising amino acid sequence SEQ ID NO:1 in the sample.

18. The method according to claim 17, wherein the method is selected from the group consisting of enzyme-linked immunosorbent assay methods, immunonephelometry methods, agglutination methods, precipitation methods, immunodiffusion methods, immunoelectrophoresis methods, immunofluorescence methods, radioimmunoassay methods, and immunohistochemistry methods.

19. The method according to claim 17, wherein the antibody or fragment thereof is detectably labeled by conjugation to a detectable moiety.

20. The method according to claim 19, wherein the detectable moiety is selected from the group consisting of radionuclides, enzymes, specific binding pair components, colloidal dye substances, fluorochromes, reducing substances, latexes, digoxigenin, metals, particulates, dansyl lysine, antibodies, protein A, protein G, electron dense materials, and chromophores.

21. The method according to claim 17, wherein the antibody or fragment thereof is attached to a substrate.

22. The method according to claim 21, wherein the substrate is selected from the group consisting of gels, hydrogels, resins, beads, nitrocellulose, nylon filters, microtiter plates, culture flasks, and polymeric materials.

23. The method according to claim 17, wherein the fragment thereof is an Fab, F(ab')$_2$, or Fv fragment of the monospecific antibody produced by the P10 hybridoma.

24. The kit for detection of fibrinogen or a fragment thereof comprising amino acid sequence SEQ ID NO:1, wherein the kit comprises:
   (a) a composition comprising a monospecific antibody produced by hybridoma cell line P10 deposited as ATCC Accession No. HB-12398, or an antigen-binding fragment thereof, that binds specifically with an epitope defined by amino acid sequence SEQ ID NO:1; and
   (b) a container housing the composition.

25. The kit according to claim 24, wherein the antibody or fragment thereof is detectably labeled by conjugation to a detectable moiety.

26. The kit according to claim 24, wherein the antibody or fragment thereof is attached to a substrate.

27. The method for diagnosing presence or probability of thrombogenesis or atherogenesis in a subject, comprising:
   (a) measuring an amount of protein comprising amino acid sequence SEQ ID NO:1 in a sample from the subject or in the subject by means of a composition comprising a monospecific antibody produced by hybridoma cell line P10 deposited as ATCC Accession No. HB-12398, or an antigen-binding fragment thereof that binds specifically with an epitope defined by the amino acid sequence SEQ ID NO:1;
   (b) comparing the measured amount of the protein in the sample from the subject or in the subject with an amount of the protein recognized to have an association with thrombogenesis or atherogenesis; and
   (c) determining from the comparison the presence or probability of thrombogenesis or atherogenesis in the subject.

28. A monospecific antibody that specifically binds with an epitope defined by amino acid sequence SEQ ID NO:1, engineered to comprise an antigen-binding fragment of a monoclonal antibody produced by hybridoima P10 (ATCC Accession No. HB-12398).

29. The monospecific antibody according to claim 28, wherein the antigen-binding fragment is an Fab, F(ab')$_2$, or Fv fragment of the monoclonal antibody produced by the P10 hybridoma.

30. The monospecific antibody according to claim 28, wherein the antibody is a synthetic, recombinant, or chimeric antibody.

31. The monospecific antibody according to claim 28, wherein the antibody is detectably labeled by conjugation to a detectable moiety.

32. The monospecific antibody according to claim 31, wherein the detectable moiety is selected from the group consisting of radionuclides, enzymes, specific binding pair components, colloidal dye substances, fluorochromes, reducing substances, latexes, digoxigenin, metals, particulates, dansyl lysine, antibodies, protein A, protein G, electron dense materials, and chromophores.

33. The monospecific antibody according to claim 28, wherein the antibody is attached to a substrate.

34. The monospecific antibody according to claim 33, wherein the substrate includes a component selected from the group consisting of gels, hydrogels, resins, beads, nitrocellulose, nylon filters, microtiter plates, culture flasks, and polymeric materials.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Gly Val Asn Asp Asn Glu Glu Gly Phe Phe Ser Ala
1               5                       10

(2) INFORMATION FOR SEQ ID NO:2:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:2:

Gln Gly Val Asn Asp Asn Glu Glu Gly Phe Phe Ser Ala
1               5                       10

(2) INFORMATION FOR SEQ ID NO:3:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: modified site
        (B) LOCATION: 1
        (D) OTHER INFORMATION: /note="pyroglutamic acid"

(xi) SEQUENCE DESCRIPTION: SEQ ID NO:3:

Xaa Gly Val Asn Asp Asn Glu Glu Gly Phe Phe Ser Ala
1               5                       10

(2) INFORMATION FOR SEQ ID NO:4:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:4:

Gln Gly Val Asn Asp Asn Glu Glu Gly Phe Phe Ser Ala Arg
1               5                       10

(2) INFORMATION FOR SEQ ID NO:5:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: modified site
        (B) LOCATION: 1
        (D) OTHER INFORMATION: /note="pyroglutamic acid"

(xi) SEQUENCE DESCRIPTION: SEQ ID NO:5:

Xaa Gly Val Asn Asp Asn Glu Glu Gly Phe Phe Ser Ala Arg
1               5                       10

(2) INFORMATION FOR SEQ ID NO:6:

(i) SEQUENCE CHARACTERISTICS:
        (A) LENGTH: 27 amino acids
        (B) TYPE: amino acid -continued ( D ) TOPOLOGY: linear ( i i ) MOLECULE TYPE: peptide ( x i ) SEQUENCE DESCRIPTION: SEQ ID NO:6:

```
Ile Glu Gly Arg Ile Ser Glu Phe Gln Gly Val Asn Asp Asn Glu
1               5                   1 0                 1 5

Glu Gly Phe Phe Ser Ala Gln Gly Val Asn Asp Asn
                2 0                  2 5
```